US012642841B2

(12) United States Patent (10) Patent No.: US 12,642,841 B2
Carpi et al. (45) Date of Patent: Jun. 2, 2026

(54) LIGANDS OF THE FSH HORMONE RECEPTOR IN THE DIAGNOSIS AND TREATMENT OF TUMORS

(71) Applicant: ONCOGREEN THERAPEUTICS SA, Lugano (CH)

(72) Inventors: Andrea Carpi, Brendola (IT); Fabio Maset, Brendola (IT); Renzo Dal Monte, Brendola (IT)

(73) Assignee: ONCOGREEN THERAPEUTICS SA, Lugano (CH)

( * ) Notice: Subject to any disclaimer, the term of this patent is extended or adjusted under 35 U.S.C. 154(b) by 1858 days.

(21) Appl. No.: 16/340,876

(22) PCT Filed: Oct. 10, 2017

(86) PCT No.: PCT/IB2017/056251
§ 371 (c)(1),
(2) Date: Apr. 10, 2019

(87) PCT Pub. No.: WO2018/069831
PCT Pub. Date: Apr. 19, 2018

(65) Prior Publication Data
US 2024/0226239 A1 Jul. 11, 2024

(30) Foreign Application Priority Data

Oct. 11, 2016 (IT) ........................ 102016000101852
Oct. 11, 2016 (IT) ........................ 102016000101862
Oct. 11, 2016 (IT) ........................ 102016000101870

(51) Int. Cl.
| | |
|---|---|
| *A61K 38/24* | (2006.01) |
| *A61K 47/64* | (2017.01) |
| *A61K 49/00* | (2006.01) |
| *A61K 51/08* | (2006.01) |
| *A61P 25/00* | (2006.01) |
| *A61P 35/00* | (2006.01) |
| *C12N 15/82* | (2006.01) |
| *C12P 21/00* | (2006.01) |

(52) U.S. Cl.
CPC .............. *A61K 38/24* (2013.01); *A61K 47/64* (2017.08); *A61K 49/0056* (2013.01); *A61K 51/08* (2013.01); *A61P 25/00* (2018.01); *A61P 35/00* (2018.01); *C12N 15/8205* (2013.01); *C12N 15/8257* (2013.01); *C12P 21/005* (2013.01)

(58) Field of Classification Search
CPC .... A61K 38/24; A61K 47/64; A61K 49/0056; A61K 51/08; A61P 25/00; A61P 35/00; C12N 15/8205; C12N 15/8257; C12P 21/005
See application file for complete search history.

(56) References Cited

FOREIGN PATENT DOCUMENTS

| | | |
|---|---|---|
| EP | 2090322 A1 | 8/2009 |
| EP | 2924049 A1 | 9/2015 |
| WO | 2014/078533 A1 | 5/2014 |
| WO | 2016/054153 A1 | 4/2016 |

OTHER PUBLICATIONS

Follicle-stimulating hormone beta-subunit [*Homo sapiens*], from https://www.ncbi.nlm.nih.gov/protein/AAB02868.1?report=genbank&log$=protalign&blast_rank=2&RID=2ZDA1N2R013, 2016, p. 1.*
Bakker et al, Follicle-Stimulating Hormone Receptor Expression and Its Potential Application for Theranostics in Subtypes of Ovarian Tumors: A Systematic Review, Cancers, 2024, 16, pp. 1-16.*
Capecitabine, from https://web.archive.org/web/20150905105447/https://www.cancer.gov/about-cancer/treatment/drugs/capecitabine, 2013, pp. 1-3.*
Wang et al., Natural compounds as anticancer agents: Experimental evidence, World J Exp Med, 2012, 2, pp. 45-57.*
Definition of cytotoxic agent, from https://www.cancer.gov/publications/dictionaries/cancer-terms/def/cytotoxic-agent, accessed 2025, p. 1.*
Transmittal of International Search Report and Written Opinion, International Patent Application PCT/IB2017/056251, mailed May 15, 2018.
Dirnberger, Dietmar et al., "Secretion of biologically active gylcoforms of bovine follicle stimulating hormone in plants," Eur. J. Biochem, 268 (2001) (10 pages).
Zhang, Xiaoyan et al., "Targeted paclitaxel nanoparticles modified with follicle-stimulating hormone β 81-95 peptide show effective antitumor activity against ovarian carcinoma," International Journal of Pharmaceutics 453 (2013) pp. 498-505.
Anonymous: "Products," Aug. 6, 2016, retrieved from internet on Jun. 9, 2017, https://web.archive.org/web/20160806105921/http://www.abres.it/product.php (2 pages).

* cited by examiner

*Primary Examiner* — Li N Komatsu
(74) *Attorney, Agent, or Firm* — Thomas Horstemeyer LLP.

(57) ABSTRACT

The present invention relates to new ligands of the follicle stimulating hormone (FSH) receptor for use in the diagnosis and treatment of neuroblastoma.

19 Claims, 21 Drawing Sheets

Specification includes a Sequence Listing.

Binary vector pABR
T-DNA Structure

*pABR*

Fig. 3
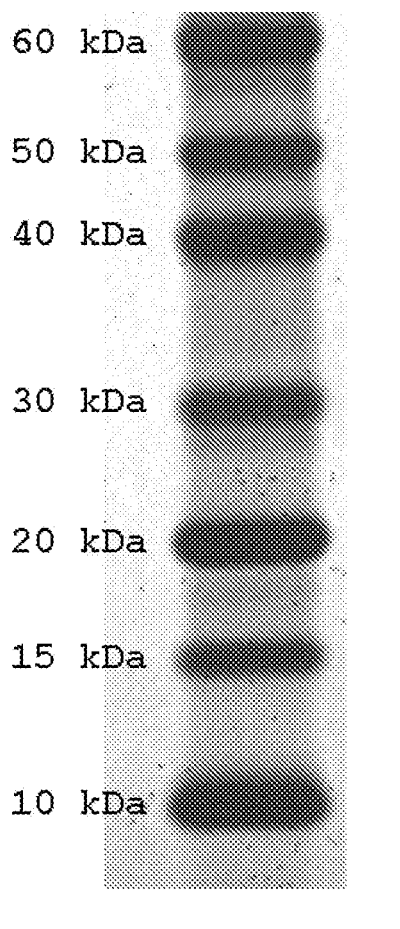
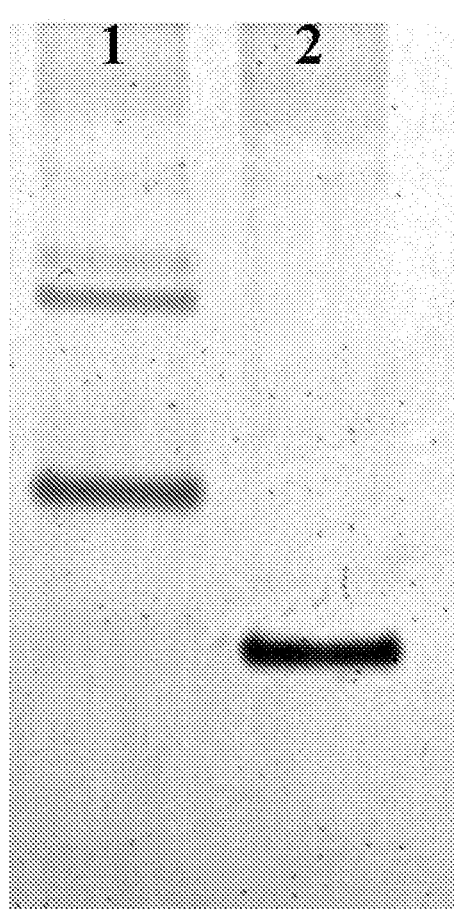

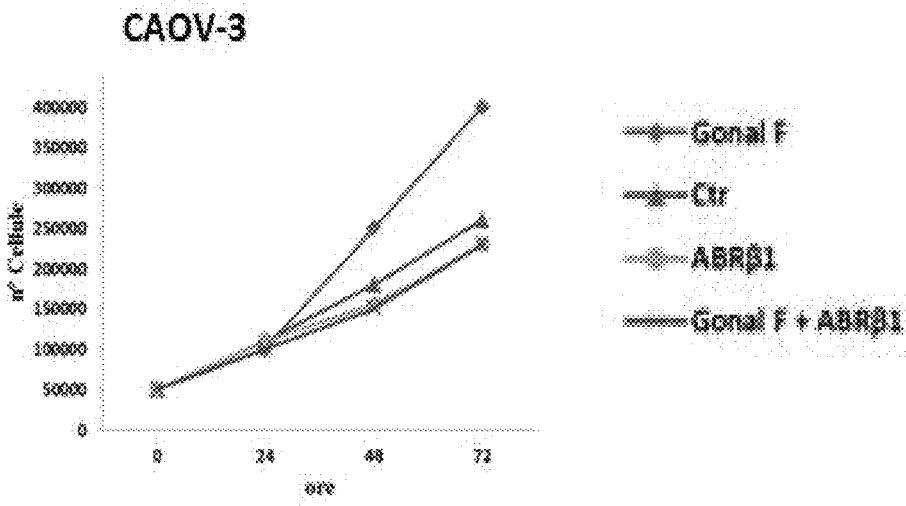
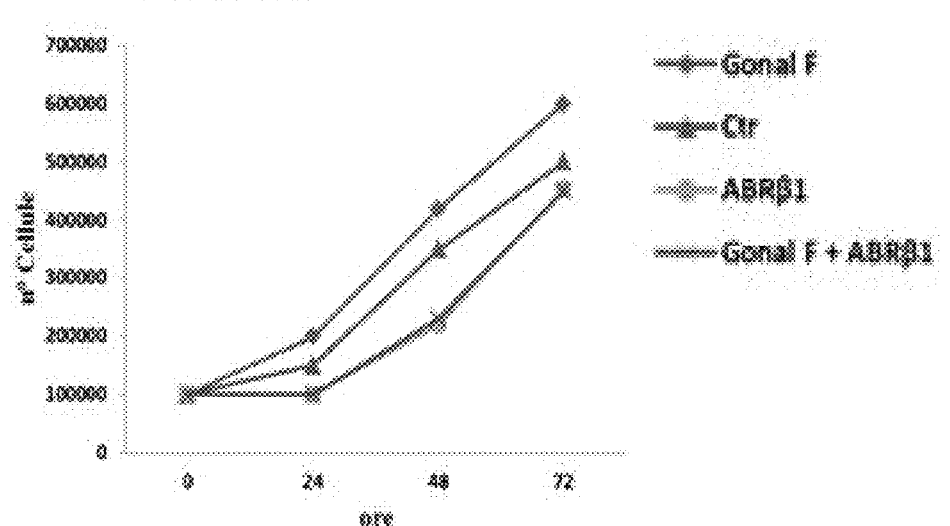
Fig. 11
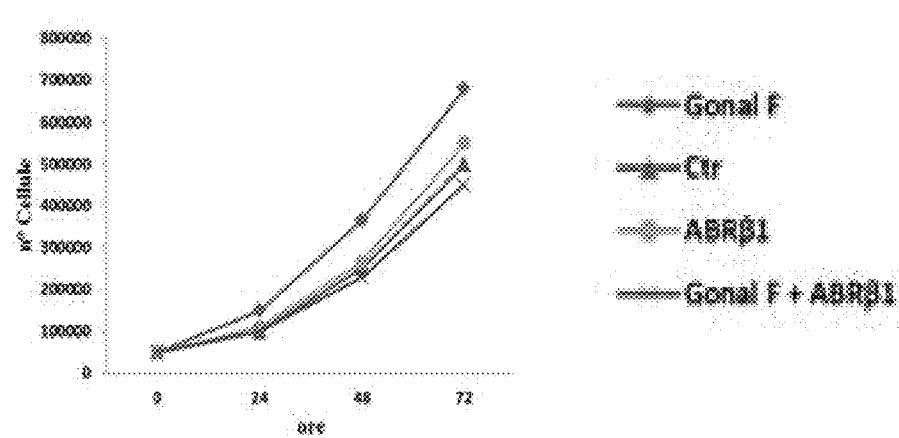

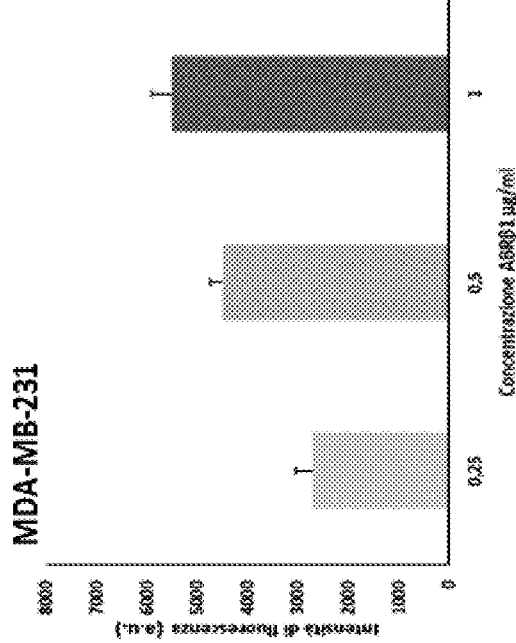
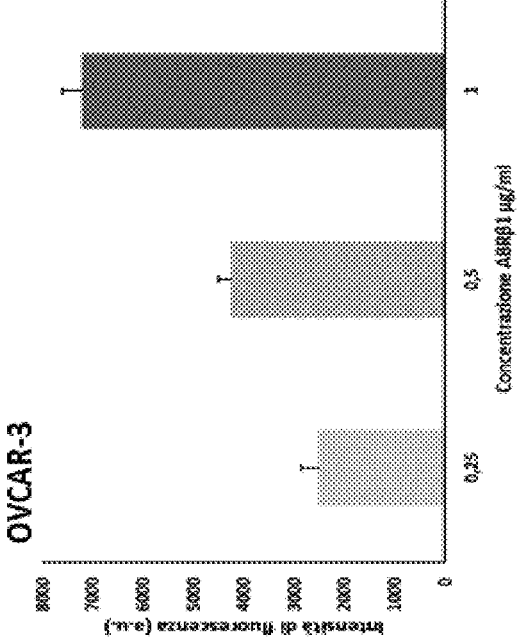
Fig. 13

Fig. 15

| Cancer tipe | FSHR expression |
|---|---|
| Ovarian | |
| *ES-2 (Ccear cell carcinoma)* | + + |
| *OVCAR-3 (adenocarcinoma)* | + + + |
| *OVCAR-5 (ascites, carcinoma)* | + + + |
| *SKOV-3 (ascites, adenocarcinoma)* | + + + |
| | |
| Triple-negative breast | |
| *MDA-MB-231 (adenocarcinoma)* | + + + |
| | |
| Ewing's sarcoma | |
| *A-673 (muscle)* | + + |
| *SK-ES-1 (bone)* | + + |
| | |
| Pancreatic | |
| *BxPC3 (adenocarcinoma)* | *//* |
| *Capan-2 (adenocarcinoma)* | *//* |
| *miaPACA-2 (carcinoma, Kras Crm)* | *//* |
| | |
| Neuroblastoma | |
| *IMR-32 (metastatic, abdominal mass)* | + + |
| *SH-SY5Y (bone marrow)* | + + + |
| | |
| Colon | |
| *LS-180 (colon, adenocacinoma)* | + + + |
| | |

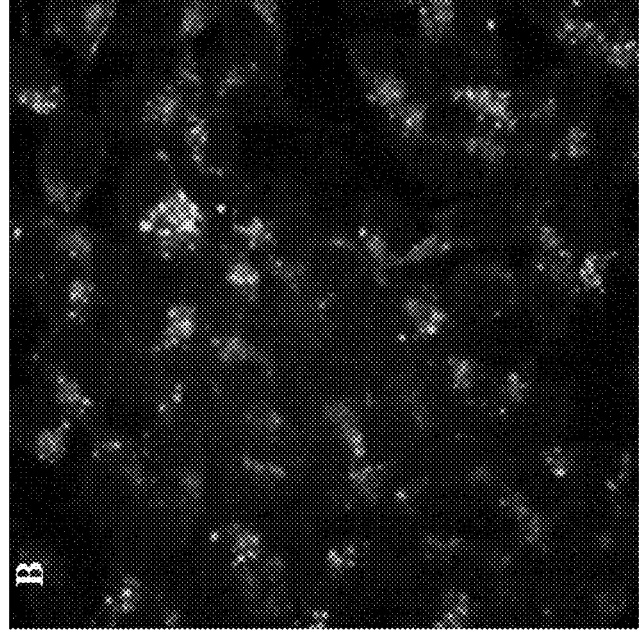
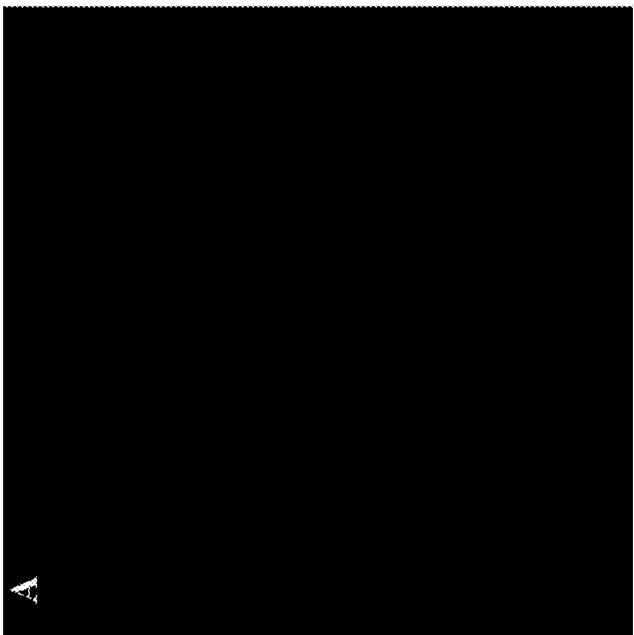
Fig. 18

| Frammento | Sequenza Corrispondente | Modificazioni | Peso Molecolare Teorico (Da) | Peso Molecolare Sperimentale (Da) | ΔPM (Da) |
|---|---|---|---|---|---|
| 1 (SEQ ID NO:5) | EECR | CAM | 592.2275 | 592.2172 | 0.0103 |
| 2 (SEQ ID NO:6) | EKDEL | (1) | 632.3017 | 632.3001 | 0.0016 |
| 3 (SEQ ID NO:7) | ELVYETVR | | 1007.5287 | 1007.54 | 0.0113 |
| 4 (SEQ ID NO:8) | IQKTCTFK | CAM (1) | 1024.5376 | 1024.5588 | 0.0212 |
| 5 (SEQ ID NO:9) | CDSDSTDCTVR | | 1200.4387 | 1200.4399 | 0.0012 |
| 6 (SEQ ID NO:10) | DLVYKDPARPK | (1) | 1300.7139 | 1300.7200 | 0.0061 |
| 7 (SEQ ID NO:11) | GLGPSYCSFGEMK | CAM(1) | 1431.6163 | 1431.6215 | 0.0182 |
| 8 (SEQ ID NO:11) | GLGPSYCSFGEMK | CAM, MSO(1) | 1447.6112 | 1447.6209 | 0.0052 |
| 9 (SEQ ID NO:12) | FQSINTTMCAGYCYTR | 1CAM | 2057.8799 | 2057.8788 | 0.0011 |
| 10 (SEQ ID NO:13) | HHHHHHNSCELTNITIAIEK | | 2370.1399 | 2370.1356 | 0.0043 |
| 11 (SEQ ID NO:14) | VPGCAHHADSLYTPVATQCHCGK | 3xCAM | 2728.1946 | 2728.1845 | 0.0101 |

SEQUENCE LISTING

```
<160> NUMBER OF SEQ ID NOS: 14

<210> SEQ ID NO 1
<211> LENGTH: 111
<212> TYPE: PRT
<213> ORGANISM: Homo sapiens

<400> SEQUENCE: 1

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 2
<211> LENGTH: 121
<212> TYPE: PRT
<213> ORGANISM: Artificial Sequence
<220> FEATURE:
<223> OTHER INFORMATION: FSHR ligand

<400> SEQUENCE: 2

His His His His His His Asn Ser Cys Glu Leu Thr Asn Ile Thr Ile
1               5                   10                  15

Ala Ile Glu Lys Glu Glu Cys Arg Phe Cys Ile Ser Ile Asn Thr Thr
            20                  25                  30

Trp Cys Ala Gly Tyr Cys Tyr Thr Arg Asp Leu Val Tyr Lys Asp Pro
        35                  40                  45

Ala Arg Pro Lys Ile Gln Lys Thr Cys Thr Phe Lys Glu Leu Val Tyr
    50                  55                  60

Glu Thr Val Arg Val Pro Gly Cys Ala His His Ala Asp Ser Leu Tyr
65                  70                  75                  80

Thr Tyr Pro Val Ala Thr Gln Cys His Cys Gly Lys Cys Asp Ser Asp
                85                  90                  95
```

Ser Thr Asp Cys Thr Val Arg Gly Leu Gly Pro Ser Tyr Cys Ser Phe
            100                     105                     110

Gly Glu Met Lys Glu Lys Asp Glu Leu
        115                 120

<210> SEQ ID NO 3
<211> LENGTH: 472
<212> TYPE: DNA
<213> ORGANISM: Artificial Sequence
<220> FEATURE:
<223> OTHER INFORMATION: synthesized

<400> SEQUENCE: 3
gaattcaaca atggctactc agagaagggc taacccatct tctcttcacc tgattaccgt        60
gttctctctg cttgtggctg tggtgtctgc tgaggtgttc catcatcacc atcatcacaa        120
ttcttgcgag ctgaccaaca tcaccattgc tatcgagaaa gaagagtgca ggttctgcat        180
cagcatcaac actacttggt gcgctggtta ctgctacacc agggatcttg tgtacaagga        240
tcctgctagg cctaagatcc aaaagacctg caccttcaaa gagctggttt acgagactgt        300
tagggtgcca ggttgtgctc atcatgctga ttctctgtac acctaccctg ttgctactca        360
gtgccattgc ggtaagtgcg atagcgattc tactgattgc accgtgagag gtctgggacc        420
ttcttactgt tctttcggtg agatgaaaga aaaggatgag ctgtagtcta ga        472

<210> SEQ ID NO 4
<211> LENGTH: 4
<212> TYPE: PRT
<213> ORGANISM: Artificial Sequence
<220> FEATURE:
<223> OTHER INFORMATION: synthesized KDEL sequence

<400> SEQUENCE: 4

Lys Asp Glu Leu
1

<210> SEQ ID NO 5
<211> LENGTH: 4
<212> TYPE: PRT
<213> ORGANISM: Artificial Sequence
<220> FEATURE:
<223> OTHER INFORMATION: synthesized EECR sequence

<400> SEQUENCE: 5

Glu Glu Cys Arg
1

<210> SEQ ID NO 6
<211> LENGTH: 5
<212> TYPE: PRT
<213> ORGANISM: Artificial Sequence
<220> FEATURE:
<223> OTHER INFORMATION: synthesized EKDEL sequence

<400> SEQUENCE: 6

Glu Lys Asp Glu Leu
1               5

<210> SEQ ID NO 7
<211> LENGTH: 8
<212> TYPE: PRT
<213> ORGANISM: Artificial Sequence
<220> FEATURE:
<223> OTHER INFORMATION: synthesized ELVYETVR sequence

```
<400> SEQUENCE: 7

Glu Leu Val Tyr Glu Thr Val Arg
1               5

<210> SEQ ID NO 8
<211> LENGTH: 8
<212> TYPE: PRT
<213> ORGANISM: Artificial Sequence
<220> FEATURE:
<223> OTHER INFORMATION: synthesized IQKTCTFK sequence

<400> SEQUENCE: 8

Ile Gln Lys Thr Cys Thr Phe Lys
1               5

<210> SEQ ID NO 9
<211> LENGTH: 11
<212> TYPE: PRT
<213> ORGANISM: Artificial Sequence
<220> FEATURE:
<223> OTHER INFORMATION: synthesized CDSDSTDCTVR sequence

<400> SEQUENCE: 9

Cys Asp Ser Asp Ser Thr Asp Cys Thr Val Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthesized DLVYKDPARPK sequence

<400> SEQUENCE: 10

Asp Leu Val Tyr Lys Asp Pro Ala Arg Pro Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: synthesized GLGPSYCSFGEMK sequence

<400> SEQUENCE: 11

Gly Leu Gly Pro Ser Tyr Cys Ser Phe Gly Glu Met Lys
1               5                   10

<210> SEQ ID NO 12
<211> LENGTH: 17
<212> TYPE: PRT
<213> ORGANISM: Artificial Sequence
<220> FEATURE:
<223> OTHER INFORMATION: synthesized FCISINTTWCAGYCYTR sequence

<400> SEQUENCE: 12

Phe Cys Ile Ser Ile Asn Thr Thr Trp Cys Ala Gly Tyr Cys Tyr Thr
1               5                   10                  15

Arg

<210> SEQ ID NO 13
<211> LENGTH: 20
<212> TYPE: PRT
<213> ORGANISM: Artificial Sequence
<220> FEATURE:
<223> OTHER INFORMATION: synthesized HHHHHHNSCELTNITIAIEK sequence
```

-continued

```
<400> SEQUENCE: 13

His His His His His His Asn Ser Cys Glu Leu Thr Asn Ile Thr Ile
1               5                   10                  15

Ala Ile Glu Lys
            20

<210> SEQ ID NO 14
<211> LENGTH: 24
<212> TYPE: PRT
<213> ORGANISM: Artificial Sequence
<220> FEATURE:
<223> OTHER INFORMATION: synthesized VPGCAHHADSLYTYPVATQCHCGK sequence

<400> SEQUENCE: 14

Val Pro Gly Cys Ala His His Ala Asp Ser Leu Tyr Thr Tyr Pro Val
1               5                   10                  15

Ala Thr Gln Cys His Cys Gly Lys
            20
```

LIGANDS OF THE FSH HORMONE RECEPTOR IN THE DIAGNOSIS AND TREATMENT OF TUMORS

CROSS-REFERENCE TO RELATED APPLICATIONS

This application is the 35 U.S.C. § 371 national stage application of PCT Application No. PCT/IB2017/056251, filed Oct. 10, 2017, where the PCT claims the priority to and benefit of Italian Patent Application No. 102016000101852, filed Oct. 11, 2016; Italian Patent Application No. 102016000101862, filed Oct. 11, 2016; and Italian Patent Application No. 102016000101870, filed Oct. 11, 2016; all of which are herein incorporated by reference in their entireties.

SEQUENCE LISTING

The official copy of the sequence listing is submitted electronically via Patent Center as a .st25 .txt formatted sequence listing with a file named "221007_1590_8125_ST25.txt", created on Aug. 1, 2025, and having a size of 5,923 bytes. The sequence listing contained in this .txt formatted document is part of the specification and is herein incorporated by reference in its entirety.

TECHNICAL FIELD OF THE INVENTION

The present invention finds application in the medical field, and in particular in the diagnosis and treatment of tumors.

BACKGROUND ART

The follicle stimulating hormone (FSH) is a glycoprotein belonging to the class of glycoprotein hormones (GPHs), which includes proteins characterized by a high structural similarity, such as the thyroid-stimulating hormone (TSH), the luteinizing hormone (LH) and chorionic gonadotropin (CG).

FSH is synthesized in the anterior pituitary gland and released into the bloodstream as a result of the gonadotropin-releasing hormone (GnRH) stimulation.

FSH plays a key role in the physiology of reproduction, inducing maturation of the ovarian follicle in women, while in men it stimulates the Sertoli cells promoting spermatogenesis (Simoni et al. 1997).

Recombinant FSH-based preparations, such as Puregon® and Gonal-F®, or of extraction from urine, such as Fostimon®, are routinely used in clinical practice to treat infertility in both women and men and in assisted procreation protocols (De Barross et al. 2013).

FSH is a heterodimer composed of two non-covalently associated subunits, α and β.

The a subunit is common to all GPHs, while the β subunit varies in different glycoprotein hormones and defines their specific biological activity.

The β subunit (UniProt code: P01225) of the human follicle stimulating hormone (FSHβ) has a molecular weight of about 12.5 kDa and consists of 111 amino acid residues of which 12 cysteine residues, involved in the formation of 6 disulfide bridges. There are two N-glycosylation sites in the protein at the level of the asparagine 7 and asparagine 24 residues.

The bioactivity of the FSH hormone depends on the glycosylation state of the asparagine 52 residue of the α chain which plays an important role in inducing the biological response.

Moreover, the glycosylation pattern at the FSHβ level influences the hormone binding capacity to the specific receptor.

Hypoglycosylated forms are provided with greater affinity for the receptor in vitro but shorter half-life times in vivo, whereas the opposite phenomenon is observed for the isoforms characterized by a complete glycosylation (Ulloa-Aguirre et al. 2011).

FSH, released in the bloodstream, is capable of reaching any district of the organism through microcirculation. FSH exerts its physiologic action through binding and activation of a specific receptor (FSH Receptor, FSHR).

Under physiological conditions, the receptor is expressed in men only in the Sertoli cells of the testes, and only in granulosa ovarian cells in women.

The FSH receptor belongs to the family of G-protein coupled receptors and the formation of the ligand-receptor complex triggers a series of cascade signals whose metabolic significance is not completely known.

The most studied physiological effect is the activation of the adenylyl cyclase enzyme which converts adenosine monophosphate (AMP) in the second messenger cyclic adenosine-monophosphate (cAMP), increasing its cytosolic concentration.

cAMP is a strong activator of the protein kinase A (PKA) which represents a key enzyme in the regulation of different processes essential to the life of the cell.

In the Sertoli cells, for example, the activation of the FSHR results in the increase of the expression of aromatase, an enzyme which converts testosterone to 17β-estradiol, stimulating the metabolic processes associated with it (Ulloa-Aguirre et al. 1998).

Already in the years 1999-2000, the scientific community began to highlight the abnormal expression of FSHR in prostate cancers but above all in ovary cancers (Ben-Josef et al. 1999; Zheng et al. 2000).

In later years, evidence to that effect increased significantly, but only in 2010 Radu and colleagues (Radu et al. 2010) demonstrated that FSHR is expressed in an abnormal manner at the level of the microcirculation endothelial tissues of many solid tumors.

Later, the evidence that in ovarian tumors, the overexpression of FSHR is correlated with the severity of the disease was consolidated; several evidences were also produced which confirmed Radu's work (Radu et al. 2010) and demonstrated that FSHR is expressed at high levels in different types of primary or metastatic solid tumors (Pawlikowski et al. 2015; Planeix et al. 2015; Siraj et al. 2013; Sardella et al. 2012; Siraj et al. 2010).

FSHR Ligands being Developed

At present, research for FSHR specific ligands follows two main methodologies: i) the development of synthetic peptides, ii) the development of monoclonal antibodies.

Both strategies have significant drawbacks such as limited specificity in the case of peptides, or inherent instability in the case of antibodies.

The molecule with the highest binding specificity for FSHR known to date is FSH, physiologically present in nanomolar (nM) concentration in the bloodstream.

It is therefore necessary to identify new and valid alternatives to existing ones, which allow to specifically reach, diagnose and treat cancers involving the FSH receptor.

The prior art document Luo S. et al. (European Journal of nuclear medicine and molecular imaging, vol. 40, no. 2, 16 Oct. 2013) describes an FSHβ subunit peptide for the diagnosis of prostate cancer. It does not describe applications for neuroblastoma.

The publication of Zhang Xiaoyan et al. (International Journal of Pharmaceutics, vol. 453, no. 2, 2013) describes the conjugation of an FSHβ subunit peptide with paclitaxel in the treatment of cancer.

The European patent application EP 2,090,322 A1 (Inst. Nat. Rech. Med.) describes a ligand of the FSHR for the imaging and the treatment of tumors which can be represented by FSH. As is known, FSH comprises two subunits (α and β)).

The European patent application EP 2,924,049 A1 describes the use of chimeric gonadotropins in the treatment of trophic hormone-related diseases.

The international patent application WO 2014/078533 A1 describes fusion constructs comprising fragments of the FSHβ subunit or the FSHβ subunit bound to a lithic domain. It does not show any evidence in the use for the treatment of neuroblastoma.

The international patent application WO 2016/054153 A1 describes a gene construct comprising a fragment of FSH or the FSHβ subunit.

The publication of Zhang et al (Cancer Research, vol. 69, no. 16, 15 Aug. 2009) describes the conjugation of paclitaxel with a fragment of the FSHβ subunit in the treatment of cancer.

SUMMARY OF THE INVENTION

The present invention is based on having surprisingly found that the β subunit of the human follicle stimulating hormone (FSHβ) is capable of binding to FSHR with high affinity.

In particular, it has been found that the β subunit of the human follicle stimulating hormone (FSHβ) can inactivate FSHR.

In addition, the inventors of the present patent application have found that forms of the FSHβ subunit obtained by employing the recombinant DNA technology can also be produced in a highly stable form.

These forms have shown to bind with high affinity to FSHR allowing special and surprising advantages.

OBJECT OF THE INVENTION

A first object of the present invention is represented by the medical use of the human follicle stimulating hormone β (FSHβ) subunit.

According to particular aspects, the human follicle stimulating hormone β (FSHβ) subunit finds application for medical use in the treatment and/or diagnosis of tumors.

In a second object thereof, the invention describes a biotechnological platform for the preparation of the β subunit of the human follicle stimulating hormone in recombinant form (ABRβ).

The β subunits of the human follicle stimulating hormone (ABRβ) obtained with such a platform are further objects of the present invention.

The medical use of these subunits, and particularly the medical use in the treatment and/or diagnosis of cancer, are further objects of the present invention.

According to another aspect, pharmaceutical preparations for administering the FSHβ and ABRβ subunits are described.

In such preparations, said FSHβ and ABRβ subunits can be conjugated with molecules having therapeutic or diagnostic activity.

The nucleotide sequences of the constructs and vectors used to obtain the described recombinant forms represent, each, further aspects of the present invention, as the novel amino acid sequences described.

In another object thereof, the present invention describes a method for the treatment and/or diagnosis of cancer comprising the use of the FSHβ or ABRβ subunits.

In a further object of the present invention, the use of the FSHβ or ABRβ subunits for the FSH (FSHR) receptor inactivation is described.

According to a further aspect of the invention, a process is described herein for preparing a ligand of the human follicle stimulating hormone (ABRβ or ABRβ1) receptor, comprising the preparation of a β subunit of the recombinant human follicle stimulating hormone (FSHβ) having a modification of the C-terminal region represented by the introduction of the KDEL sequence (SEQ ID NO:4).

In a particular aspect, such a process may further comprise the modification at the N-terminal end of the sequence of the β subunit of the human follicle stimulating hormone (FSHβ) represented by the introduction of a His-tag.

Therefore, the use of the KDEL sequence (SEQ ID NO:4) at the C-terminal end and possibly the use of a His-tag at the N-terminal end of the sequence of the β subunit of the human follicle stimulating hormone (FSHβ) for preparing ligands of the human follicle stimulating hormone (FSHβ) receptor represent further objects of the present invention.

BRIEF DESCRIPTION OF THE FIGURES

FIG. 3 shows the SDS-PAGE analysis after deglycosylation of purified ABRβ1;

FIG. 11 shows the effect of the ligand ABRβ1 on the growth of cancer cells;

FIG. 13 shows the results of the analysis of internalization of the ligand ABRβ1 in cancer cells performed with flow cytometry technique;

FIG. 15 shows the result of the expression analysis of FSHR by immunoflow cytometry technique in a panel of human cancer cells;

FIG. 18 shows the results of the analysis of internalization of ABRβ1 labeled with NBD in NB3 cells (a fraction higher than 96% of treated cells shows the appearance of signal localized in cytoplasmic vesicles (panel B) (n=3). Untreated cells (Panel A));

FIG. 19 shows the amino acid sequence coverage through mass spectrometry analysis of the deglycosylated form of the ligand ABRβ1 subjected to tryptic digestion (CAM: carbamido-methylcysteine; (1): missed cleavage; MSO: methionine sulfoxide);

DETAILED DESCRIPTION OF THE INVENTION

Definitions

Figure 1:
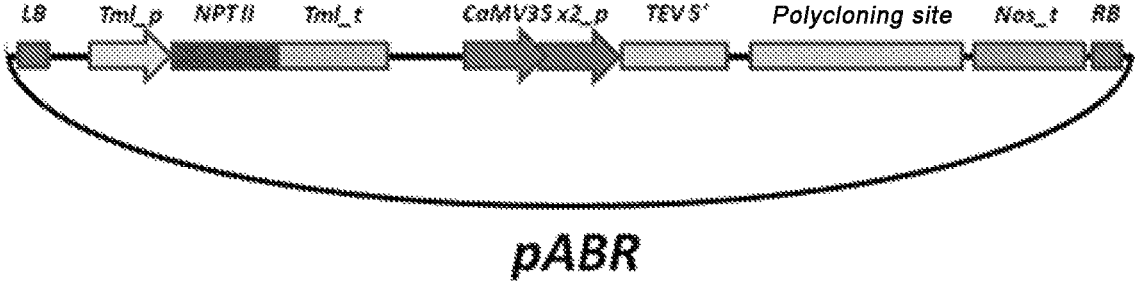
FIG. 1 shows the structure of the binary vector pABR: RB/LB, specific recombination sites, left edge and right edge; Tml_p, promoter of the tumor morphologylarge DNA; NPT II, neomycin phosphotransferase II; Tml_t, terminator of the tumor morphologylarge DNA; CaMV35x2_p, promoter of the cauliflower mosaicvirus; TEV 5', untranslated TEV sequence; Nos_t, terminator of the nopalyne synthase.

In the present description of the invention, where not otherwise indicated, the terms shall be understood as having the meaning set forth hereinafter.

"FSHR" means the human follicle stimulating hormone (FSH) receptor; this hormone includes the two α and β subunits.

"FSHβ" means the single beta subunit of the human follicle stimulating hormone (FSH); this subunit is characterized by the sequence corresponding to SEQ ID NO:1.

"ABRβ" means the beta subunits of the human follicle stimulating hormone (FSH) obtainable by using a biotechnological platform according to the present invention.

"ABRβ1" means a specific beta subunit of the human follicle stimulating hormone (FSH) obtained by using the biotechnological platform for the production in plant cells of *Nicotiana benthamiana* according to the present invention; this subunit is characterized by the amino acid sequence corresponding to SEQ ID NO:2.

More generally, the FSHβ, ABRβ and ABRβ1 subunits may be referred to as "ligand" of the FSHR receptor as they are capable of binding to the receptor itself.

According to a first object of the present invention, the medical use of the β subunit of the human follicle stimulating hormone (FSHβ) is described.

In particular, the present invention describes the use of the β subunit of the human follicle stimulating hormone (FSHβ) in the treatment and/or diagnosis of cancer.

The term cancer refers to tumor and cancer, i.e. those tissues characterized by an abnormal growth caused by an uncontrolled cellular multiplication.

In a preferred aspect, such a tumor or cancer is a primary or metastatic solid tumor.

In detail, prostate (in particular prostate adenocarcinoma), mammary gland, colon, pancreas, kidney, lung, liver, testis, ovary, brain and thyroid tumors and cancers are included; sarcomas are also included.

According to an aspect of the invention, such a medical use may find application in the treatment of infant neuroblastoma.

In particular, such a medical use is described in pediatric patients and, preferably, in patients up to 6 years of age.

For the purposes of the present invention, the FSHβ subunit is used in cancer therapy as such or combined with anticancer agents.

In the form not conjugated to any drug, the FSHβ subunit may be used as an FSH competitor in the binding with FSHR and thus capable of blocking the activity of the receptor.

As for the anticancer drugs which can be used and conjugated to the β subunits, these may belong to:

the class of cytotoxic agents. Preferably, such compounds are selected from the group comprising: pyrimidine antagonists, such as capecitabine, enzyme inhibitors, such as the camptothecins family, for example irinotecan;

the class of alkylating agents. Preferably, such compounds are selected from the group comprising: the metal salts family, such as cisplatin, DNA intercalators, such as doxorubicin, the anthracycline family;

the class of protein synthesis modulators. Preferably, such compounds are selected from the group comprising: the proteasome inhibitors family, such as bortezomib, the mTOR inhibitors family, such as temsirolimus;

the class of mitotic inhibitors.

Preferably, such compounds are selected from the group comprising: the ansamitocin family, such as maytansine, the microtubule polymerization inhibitors family, such as auristatin E;

the class of β-emitting radioisotopes. Preferably, such compounds are selected from the group comprising: $^{131}I$, $^{169}Er$, $^{77}Lu$, $^{186}Re$, $^{153}Sm$, $^{89}Sr$ and $^{90}Y$.

According to an aspect of the invention, the FSHβ subunit is used in the diagnosis of tumors.

In particular, they are the tumors and cancers mentioned above.

Once suitably conjugated, the FSHβ subunit therefore allows the detection in diagnostic imaging in oncology.

The techniques used to this end include, for example: Positron Emission Tomography (PET), Nuclear Magnetic Resonance (NMR), Single Photon Emission Tomography (SPECT) and ultrasound; therefore, the FSHβ subunit can be suitably conjugated with molecules suitable for diagnosis using techniques such as: Positron Emission Tomography (PET), Nuclear Magnetic Resonance (NMR), Single Photon Emission Tomography (SPECT) and ultrasound.

For the present purposes, the term diagnosis also refers to the ability of checking the tumor progression over time and/or its progression or regression during a therapeutic treatment.

For the purposes of the present invention, diagnosis also means using the FSHβ subunit to conduct in vitro analysis for laboratory purposes.

According to a first aspect, the FSHβ subunit may be suitably conjugated with fluorescent molecules such as: fluorescein isothiocyanate (FITC), phycoerythrin (PE) or indocyanine (Cy5).

In the field of nuclear medicine, the FSHβ subunits may be conjugated with radioactive molecules such as: [123]I, $^{111}$In, [188]Re, $^{18}$F, $^{35}$S, [99]Tc.

In a particular aspect, the FSHβ subunit may also be conjugated with nanoparticles of a different nature.

The conjugation with nanoparticles may be through a suitable linker.

Nanoparticles

The nanoparticles used in medicine as carriers (for example for drugs, radioisotopes, fluorescent molecules or enzymes) usually have a size of between 1 nm and 1 μm.

The nanoparticles may have smooth or uneven surface, may be solid, hollow, crossed by canaliculi or consisting of lenticular structures.

Nanoparticles are particles made of inorganic or organic materials; inorganic-based ones may consist of Au, Ag, Si, Se, Cd or carbon compounds, such as graphene, while those of organic origin may consist, for example, of polymers of sugars or lipids (micelles, liposomes) or molecules such as poly(lactic-co-glycolic) acid (PLGA).

The purpose of nanoparticles is to convey a large amount of molecules contained within them to the reference site.

For the purposes of the present invention, the term "conjugated" means that the FSHβ subunit or an ABRβ subunit or, more specifically, an ABRβ1 subunit is suitably linked to a molecule with diagnostic or therapeutic activity.

Such a bond, in particular, may be represented by a covalent chemical bond, directed or obtained by a suitable linker, or by a coordination bond.

As for the origin of the FSHβ subunit, this can be obtained from the purification of human urine or using recombinant DNA techniques; it can also be obtained from commercial products such as Fertinex®, Metrodin HP®, Gonal-F® (Serono), Follistim®, Puregon® (Merk Sharp & Dohme).

According to another aspect of the invention, the FSHβ subunit, in the conjugated form or in the non-conjugated form with molecules having therapeutic activity, is used in a method for the treatment of tumors in combination with a therapeutic agent (combo therapy).

The combination of the FSHβ subunit with the therapeutic agent is capable of providing a synergistic effect.

Such a therapeutic agent may be selected from the group of molecules used in the treatment of the specific form of cancer.

In a second object, the invention describes a biotechnological platform for the preparation of the β subunit of the human follicle stimulating hormone from plant cells and, more specifically, from Nicotiana benthamiana (ABRβ1).

More generally, the biotechnological platform uses a process whereby the amino acid sequence of the FSHβ subunit is suitably modified so as to insert a signal peptide characteristic of the plant cells for the directing to the endoplasmic reticulum.

The present invention therefore uses the KDEL sequence (SEQ ID NO:4) to modify the C-terminal region of the β subunit of the human follicle stimulating hormone (FSHβ), particularly in order to keep the protein in the endoplasmic reticulum.

The resulting protein therefore undergoes a peculiar glycosylation process, which surprisingly leaves the processes which guide the protein folding unchanged.

In particular, the ABRβ1 ligand of the present invention is glycosylated to the asparagine residues 13 and 30 of the mature protein.

More in detail, the glycosylation sites include branched structures of mannose residues.

Mannose residues are in a total number of about 45-75, preferably about 50-70 and even more preferably about 58-62, where they can be 60 or 61.

Each glycosylation site includes two N-acetylglucosamine residues and a branched structure of mannose residues.

In particular, each branched structure includes 29, 30 or 31 mannose residues.

Each mannose residue may include phosphorylation, sulforylation or methylation.

Moreover, the polysaccharide portions may be bound to molecules comprising phenol groups.

Molecules comprising phenol groups are characteristic of plant cells.

In particular, such phenol groups are typical of the plant cells of Nicotiana benthamiana.

In a particular aspect, the object of the present invention is the FSHβ subunit (ABRβ1) obtained with the process described herein.

In particular, such a process comprises the modification at the C-terminal end with the KDEL sequence (SEQ ID NO:4) and at the N-terminal end with a 6 His-tags of the β subunit of the human follicle stimulating hormone (FSHβ).

The platform described by the present invention therefore uses the KDEL sequence (SEQ ID NO:4) at the C-terminal end and possibly also uses the of a His-tag at the N-terminal end of the sequence of the β subunit of the human follicle stimulating hormone (FSHβ) for the preparation of ligands of the human follicle stimulating hormone receptor (FHSR).

Therefore, according to a preferred aspect, the present invention describes a process for the preparation of a recombinant form of the β subunit of the follicle stimulating hormone (FSH) comprising the steps of:

I) obtaining a suitable vector transformed with a plasmid containing the sequence corresponding to SEQ ID NO:3;

II) transforming the Nicotiana benthamiana cells with the vector of step I);

III) selecting the transformed Nicotiana benthamiana cells;

IV) growing the stable Nicotiana benthamiana cells;

V) preparing a cellular extract;

VI) purifying an FSHR receptor ligand.

In a preferred aspect, the vector of step I) is represented by Agrobacterium tumefaciens.

In particular, in step II), the transformation is carried out for 48 hours co-culture in the dark at about 25° C. and under constant stirring.

Thereafter, the cells are selected.

Preferably, in step III), a selection medium is used which comprises: MS supplemented with 0.9% w/v agar and antibiotics.

In a preferred aspect, the following are used for this purpose: carbenicillin and kanamycin, more preferably 250 mg/L carbenicillin and 100 mg/L kanamycin.

In a preferred aspect of the invention, in step V), the Nicotiana benthamiana cells are cultured in suspension.

In another preferred aspect, the culture provides for an initial inoculation of Nicotiana benthamiana cells equal to 10% of the final culture volume.

The cellular culture is maintained in incubation in the MS medium (Murashige 1962) supplemented with sucrose, naphthalene-acetic acid (NAA) and kinetin for a period of 15 days at 24-27° C. and maintaining an aeration of 50-100 mbar.

In addition, sub-cultures are prepared every 7 days by transferring an aliquot of cell suspension in the fresh medium.

The cells are incubated under stirring, in the dark and at a constant temperature of 25° C.

According to the present invention, step V) includes the use of an extraction buffer containing: 50 mM $Na_2HPO_4$, 150 mM NaCl, 20 mM citric acid, 40 mM ascorbic acid, 5 mM EDTA, 1 mM PMSF, 0.05% (v/v) TWEEN-20 (non-ionic detergent), pH 6.5 supplemented with 1% (w/v) XAD-4 and 1% (w/v) polyvinylpolypyrrolidone (PVPP).

Thereafter, ammonium sulfate is added to the extract up to obtaining a 70% saturation concentration, incubated at 4° C. for 1 hour under constant stirring.

The precipitate is then recovered by centrifugation and resuspended in an IMAC buffer.

The preparation is centrifuged and filtered.

The resulting solution is purified in a step VI) by passages on a column.

In particular, the solution is loaded on an IMAC chromatography column.

Preferably, an Ni Sepharose 6 FF column is used.

Subsequently, the fractions of interest are combined and loaded on a desalting column.

Preferably, a Sephadex G-25 Medium column is used.

Subsequently, the fractions of interest are combined and loaded on a ion exchange chromatography column.

Preferably, an SP Sepharose HP column is used.

During the purification, the absorbance is monitored at 280 and 254 nm.

As described above, the β subunit of the human follicle stimulating hormone (FSHβ) obtained according to the method described herein (ABRβ1) and the medical use hereof in the treatment and/or diagnosis of tumors are further objects of the present invention.

In particular, the present invention describes the use of the ABRβ subunit in the treatment and/or diagnosis of cancer.

The term cancer refers to tumor and cancer, i.e. those tissues characterized by an abnormal growth caused by an uncontrolled cellular multiplication.

In a preferred aspect, such a tumor or cancer is a primary or metastatic solid tumor.

In detail, prostate, mammary gland, colon, pancreas, kidney, lung, liver, testis, ovary, brain and thyroid tumors and cancers are included; sarcomas are also included.

According to an aspect of the invention, such a medical use may find application in the treatment of infant neuroblastoma.

In particular, such a medical use is described in pediatric patients and, preferably, in patients up to 6 years of age.

As described above, the ABRβ1 subunit is obtained by biotechnological route from the cultivation of plant cells of *Nicotiana benthamiana* in suspension.

According to alternative aspects of the present invention, the ABRβ subunit may be obtained by biotechnological route in other cells, such as in mammalian, yeast, bacteria cells or other plant cells.

In particular, among the plant cells, *Daucus carota, Oryza sativa, Glycine max*, Maize cells, etc., may be used.

According to another aspect, pharmaceutical preparations for administering the FSHβ and ABRβ subunits and, more particularly, the ABRβ1 subunits, are described.

More specifically, such preparations may include the FSHβ subunit or an ABRβ subunit or, more specifically, an ABRβ1 subunit and one or more pharmaceutically acceptable carriers and/or excipients.

Such subunits, in preferred aspects of the invention, may be conjugated with suitable molecules having therapeutic or diagnostic activity, as described above with reference to the FSHβ subunit.

According to another aspect of the invention, the ABRβ1 subunit, in the conjugated form or in the non-conjugated form with molecules having therapeutic activity, is also used in a method for the treatment of cancer in combination with a therapeutic agent (combo therapy).

The combination of the ABRβ1 subunit with the therapeutic agent is capable of providing a synergistic effect.

Such a therapeutic agent may be selected from the group of molecules used in the treatment of the specific form of cancer.

Therefore, the present invention provides diagnostic and therapeutic formulations comprising the ABRβ1, FSHβ subunits described above or other ABRβ subunits (obtainable with the recombinant DNA technology applied to other cells).

More specifically, such preparations are formulated for intravenous administration.

According to a further object, the present invention describes a method for the treatment and/or for the diagnosis of tumors comprising the use of the FSHβ, ABRβ1 subunit or other ABRβ subunits.

In particular, such a method comprises the step of administering, to a patient in need thereof, a pharmaceutically effective amount of the FSHβ or ABRβ or ABRβ1 subunits possibly formulated in a suitable pharmaceutical preparation.

For the present purposes, a patient is intended to be a subject suffering from a primary or metastatic solid tumor.

In detail, prostate (in particular prostate adenocarcinoma), mammary gland, colon, pancreas, kidney, lung, liver, testis, ovary, brain and thyroid tumors and cancers are included; sarcomas are also included.

According to a particular aspect, such a method may find application in the treatment of infant neuroblastoma.

In particular, such a medical use is described in pediatric patients and, preferably, in patients up to 6 years of age.

Diagnostic method also refers to the ability of checking the tumor progression over time and/or its progression or regression during a therapeutic treatment.

In other words, reference is made to a method for checking the progression of a tumor over time and/or its progression or regression during a therapeutic treatment comprising the steps of determining the extent of the tumor in a subject at different and subsequent times (such as a time $t_0$ and a time $t_1$), wherein between said times (such as $t_0$ and $t_1$) a tumor treatment step may be conducted.

The present invention provides a method for the in vivo inactivation of the FSHR receptor comprising the step of administering a pharmaceutically active amount of the FSHβ or ABRβ or ABRβ1 subunit.

Such a method may alternately be carried out in vitro in the laboratory for different purposes.

According to a further aspect of the present invention, the use of the FSHβ or ABRβ or ABRβ1 subunit for inactivating the FSHR receptor is described.

Such an inactivation, in particular, can be conducted in vivo or in vitro.

Therefore in the present patent application, the following sequences are described:

| | |
|---|---|
| SEQ ID NO: 1 | Sequence of the human FSHβ subunit |
| SEQ ID NO: 2 | ABRβ1 sequence |
| SEQ ID NO: 3 | ABRβ1 encoding sequence |

With reference to the sequence of the ABRβ1 subunit, all sequences which have a similarity with SEQ ID NO:2 such as to not modify the interaction with the FSHR receptor are intended to be comprised in the objects of the present invention.

In particular, by "similarity" it is meant the percentage of amino acids occupying the same position which can be substituted with a different or structurally equivalent amino acid, where a similarity equal to 100% means that the two sequences are identical.

The similarity may be determined by alignment, conducted in particular according to one or more known algorithms or programs, such as CLUSTALW or BLAST.

In a preferred aspect of the invention, the percentage of similarity is in reference only to the sequence of the ABRβ1 subunit in common with the sequence of the FSHβ subunit.

In another preferred aspect of the invention, the percentage of similarity is in reference only to the amino acids of the portions of the sequence of ABRβ1 which do not include the amino acids involved in the interaction with the receptor.

The amino acids of the ABRβ1 involved in the interaction with the receptor correspond to amino acids 33-53 of the FSHβ sequence.

For the purposes of the present invention, the similarity is greater than about 90%, preferably it is between about 90-99.9% and more preferably between about 95-97%.

EXPERIMENTAL PART

1. Production and Purification of the ABR Ligand

The protein sequence of human FSHβ (UniProt: P01225) was modified in silico as described in the following section relating to materials and methods. The gene sequence encoding for the novel protein, including the signal peptide region (ABRβ1 ligand) was optimized for the expression in plants (SEQ ID NO:3).

The nucleotide sequence was then inserted into the binary vector pABR expression cassette (FIG. 1) and using *Agrobacterium tumefaciens* as plant cell transformation system, the stable clones of *Nicotiana benthamiana* expressing the highest level of the ABRβ1 ligand were obtained and selected.

The ABRβ1 ligand was purified from plant cells cultured in suspension using sequential chromatographies.

2. Chemical Characterization of the ABRβ1 Ligand

The ABRβ1 ligand obtained after optimizing the purification process was analyzed using SDS-PAGE electrophoresis.

The immunoblotting analysis with human FSHβ specific antibody and polyacrylamide gels subjected to staining with Coomassie Brilliant Blue or with the more sensitive silver staining show that the ABRβ1 ligand achieves a purity level of 95-98%. The analysis reveals the existence of two reactive species to the FSHβ antibody.

Figure 2:
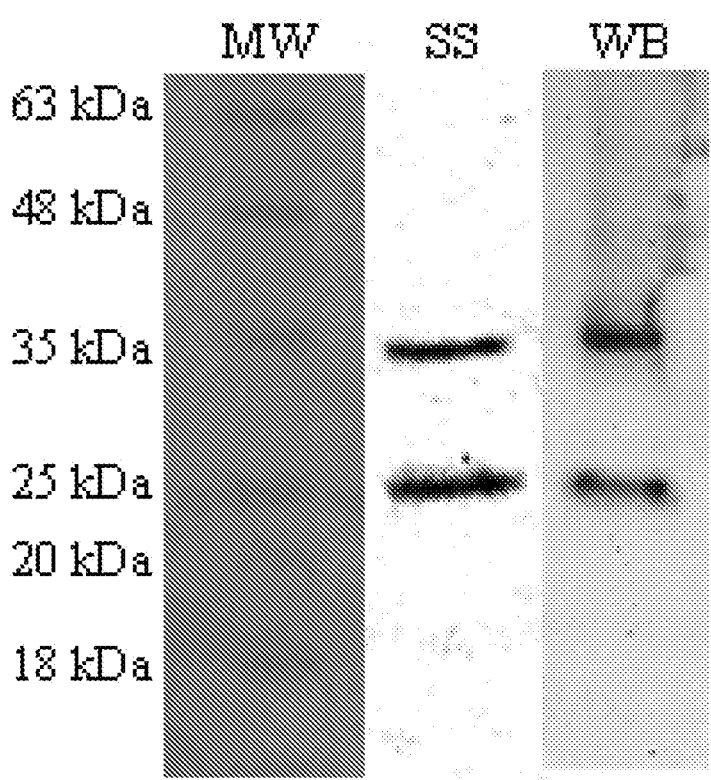
FIG. 2 shows the results of the electrophoretic analysis of purified ABRβ1.

FIG. 2 shows the results of the electrophoretic analysis of purified ABRμ1. 0.1 μg of purified ABRβ1 are analyzed in SDS-PAGE. MW molecular weight marker; SS, silver staining; WB, immunoblotting using human FSHβ specific antibody. The forms at 25 and 37 kDa detected by silver staining are reactive to the human FSHβ specific antibody. The two species of apparent molecular weight of 25 kDa and 37 kDa are the result of the different protein glycosylation pattern.

The treatment of the sample with a glycosylase (PNGase F) produces the disappearance of the two high molecular weight species into a single form of apparent molecular weight of 14 kDa.

FIG. 3 shows the SDS-PAGE analysis results after deglycosylation of purified ABRβ1. 0.1 μg of purified ABRβ1 were subjected to deglycosylation protocol and analyzed in SDS-PAGE and subsequent silver staining. To the left, molecular weight marker; 1, ABRβ1 ligand purified and not deglycosylated; 2, ABRβ1 ligand purified and subjected to deglycosylation. The glycosylated forms at 25 and 37 kDa disappear after deglycosylation and the generation of a non-deglycosylated form having apparent weight of 14 kDa is observed.

All the molecular species were analyzed with different mass spectrometry techniques to determine the accurate molecular weight and the amino acid sequence thereof. The glycosylated species were assigned a molecular weight of 24493.2 Da and 37654.57 Da, respectively, the deglycosylated protein has a molecular weight of 13783.6 Da.

The protein fingerprint analysis showed that the amino acid sequence of the ABRβ1 ligand is identical to that of mature human FSHβ with the modifications made as described in the present patent application (FIG. 19).

Since the tertiary structure is essential to the efficient linkage with FSHR, the assembly pattern of the disulfide bonds of the ABRβ1 ligand was verified. The mass spectrometry analysis of samples obtained by partial proteolysis of the ABRβ1 ligand allowed the identification of the cysteine pairs involved in the formation of disulfide bonds. The identification of the cysteine pairs involved in the formation of disulfide bonds shows a pattern identical to that observed in mature human FSHβ, confirming that the ABRβ1 ligand has the correct protein folding.

3. Glycosylation

The ABRβ1 ligand has the KDEL amino acid sequence (SEQ ID NO:4) at the C-terminal. Considering the molecular weight of the two glycosylated protein forms and of the deglycosylated one, the mass of the glucose portion in the proteins can be derived. Assuming that in the two asparagine residues present in the same protein form the glycosylation pattern similar, we may infer that in the 24493 Da protein there is a first glucose portion consisting of N-acetylglucosamine and 30 mannose residues and a second glucose portion consisting of 2 N-acetylglucosamine and 31 mannose residues. In the 37654 protein form there is a glucose portion consisting of N-acetylglucosamine and 70 mannose residues and a second glucose portion consisting of 2 N-acetylglucosamine and 71 mannose residues.

Figure 4:
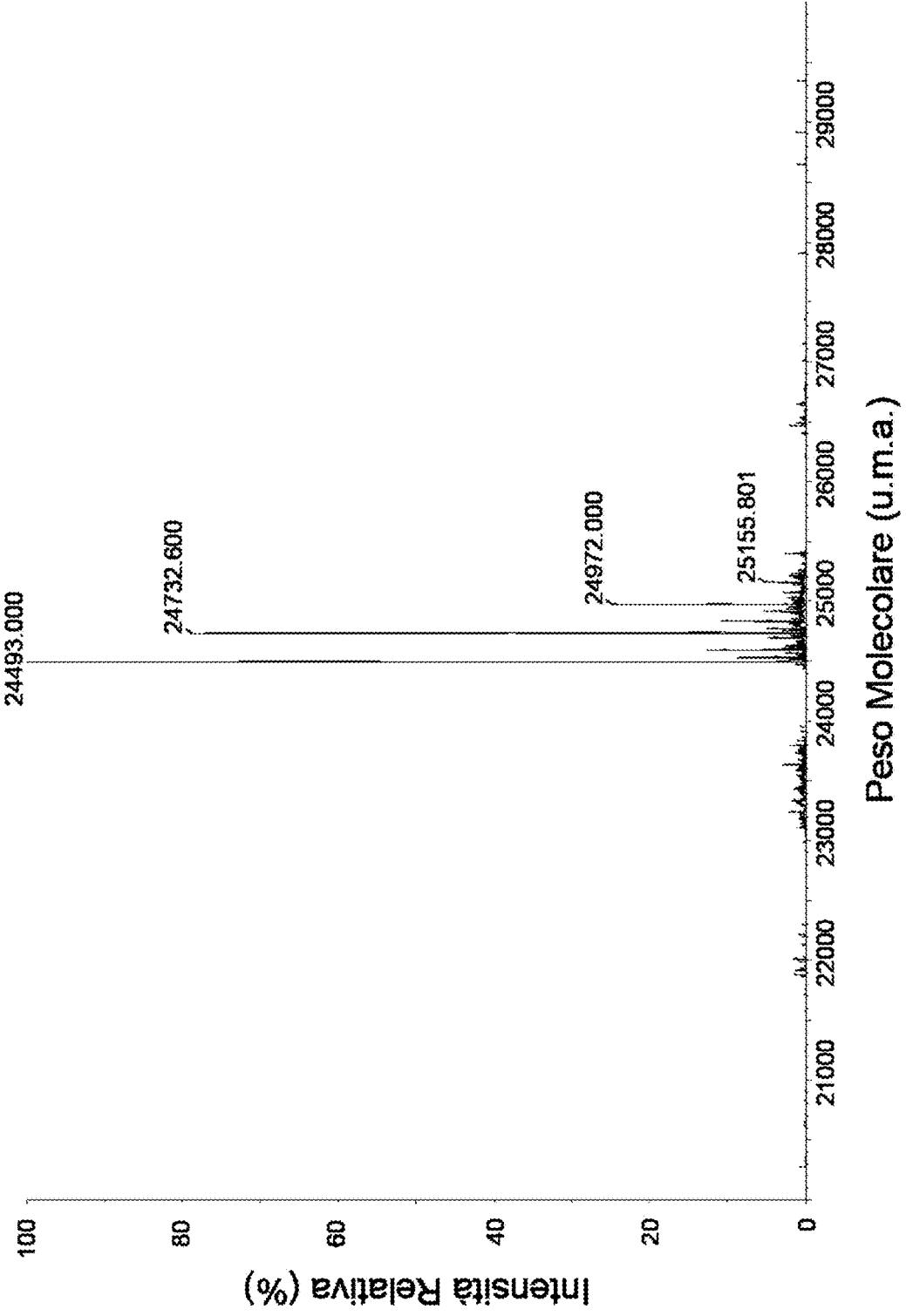
FIG. 4 shows the mass spectrum of purified ABRβ1 (band at 25 kDa)

In a second step of the production and purification process of the ABRβ1 ligand, the cell culture conditions were modified in order to achieve the process optimization and the production of a single and particular form of glycosylated ABRβ1. The only form of ABRβ1 thus obtained has a molecular weight of the deglycosylated amino acid sequence of 13783.6. In the band corresponding to the glycosylated form of 24493 there are 3 glycosylation isoforms which differ from each other due to the presence of one or two mannose phosphate residues, as shown by the mass spectrometry analysis (FIG. 4). This hyperglycosylation arrangement is completely unexpected and extremely different from the glycosylation pattern in mammalian cells, and in particular in humans.

4. Stability and Aggregation

In order to verify the stability and the tendency to aggregate of the ABRβ1 ligand, the purified protein was subjected to three freeze/thaw cycles, cryo-freeze drying under vacuum or incubation at 20° C. and 37° C. for 72 hours. The aggregation assessment was conducted using the size exclusion chromatography (SEC) technique in HPLC.

The analysis revealed that the aggregated protein percentage with respect to the total protein in the ABRβ1 ligand at the end of the purification process is less than 4%.

Figure 5:
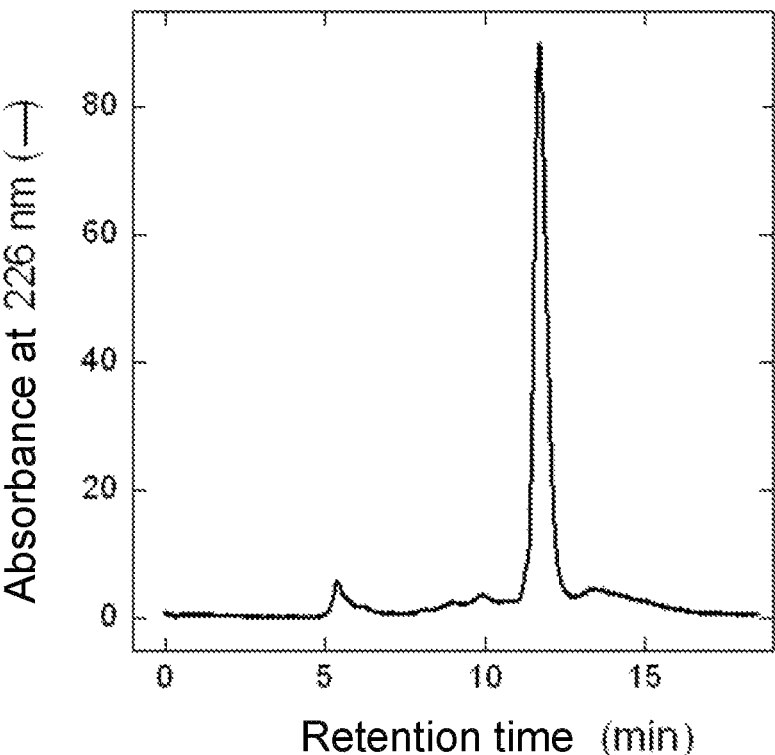
FIG. 5 shows the results of the analysis of the aggregation state of the ligand ABRβ1 through size exclusion chromatography in HPLC.

FIG. 5 shows the results of the analysis of the aggregation state of the ABRβ1 ligand through size exclusion chromatography in HPLC; The ABRβ1 ligand shows a chromatographic profile with the presence of one main peak only, corresponding to the soluble forms. The analysis of the areas under the peaks shows an aggregation lower than 4% in all samples analyzed (n=3, p≤0.05).

Figure 6:
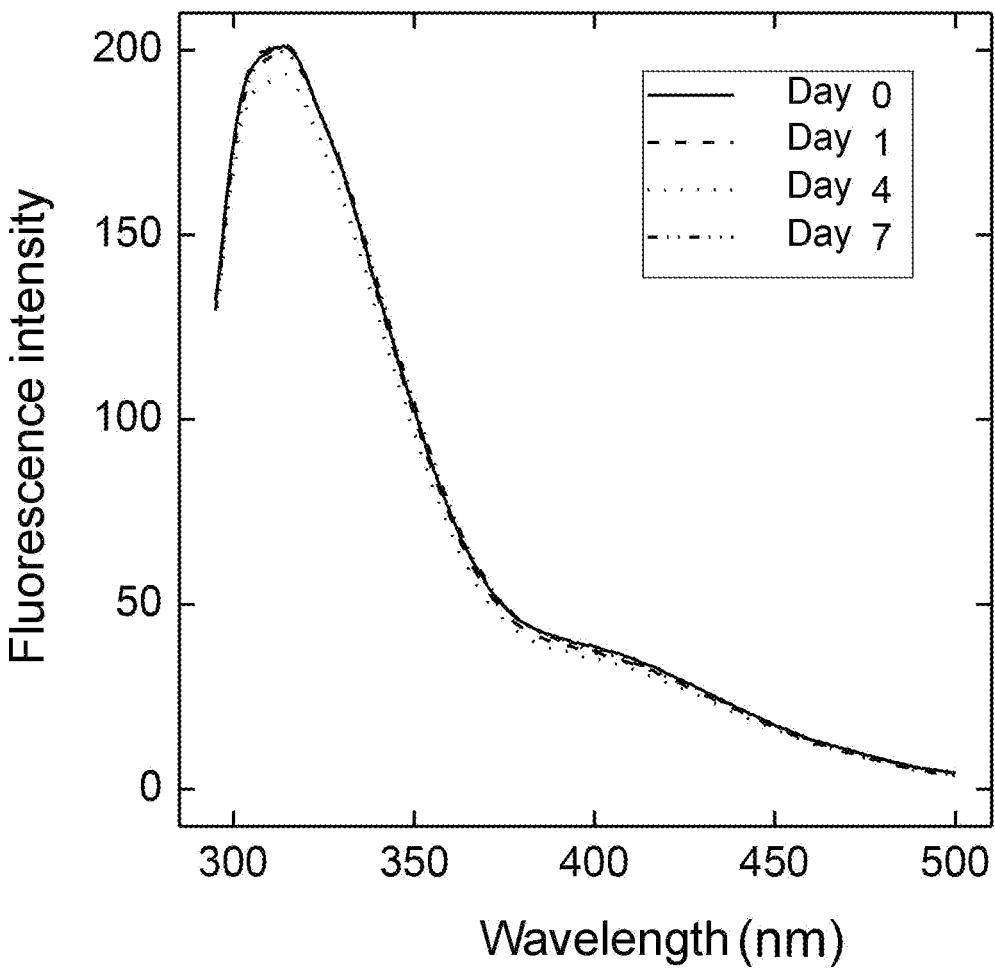
FIG. 6 shows the results of the stability analysis of the ligand ABRβ1 by fluorimetric technique.

The stability of the purified ABRβ1 ligand and in solution over time was analyzed by fluorimetric technique. An aliquot of ABRβ1 was thawed and brought to a final volume of 1600 μl (1 μM conc. With 20 mM HEPES buffer, pH 7.4, 0.15 M NaCl, 0.1% PEG-8000 (w/v). The sample was then immediately analyzed and subsequently stored in refrigerator at 4° C. The sample was reanalyzed over time, measuring and recording the fluorescence emission spectrum. As shown in FIG. 6, the fluorescence spectrum characteristics of ABRβ1 do not change over time up to 7 days from the first analysis.

The samples of purified protein, subjected to the treatments described above, show no significant variations in the percentage of aggregation, indicating that the protein in such conditions is characterized by excellent solubility and stability over time.

5. Effect of the ABRβ1 Ligand on the Activation of the FSHR Receptor in Sertoli Cells.

Sertoli cells represent the model of choice for the study of the FSH and the activation of FSHR "in vitro". In these cells, the activation of FSHR induces an increase in the expression of the aromatase enzyme, which converts testosterone to estradiol. The increase of estradiol produced thus represents an important parameter to determine whether a molecule is capable of activating FSHR. In this model, Gonal-F® induces the increase in the production of estradiol by about 300% with respect to untreated cells. Surprisingly, in the same experimental conditions, the ABRβ1 ligand does not cause any change in the estradiol production, thus proving the complete inability to activate the FSHR.

Figure 7:
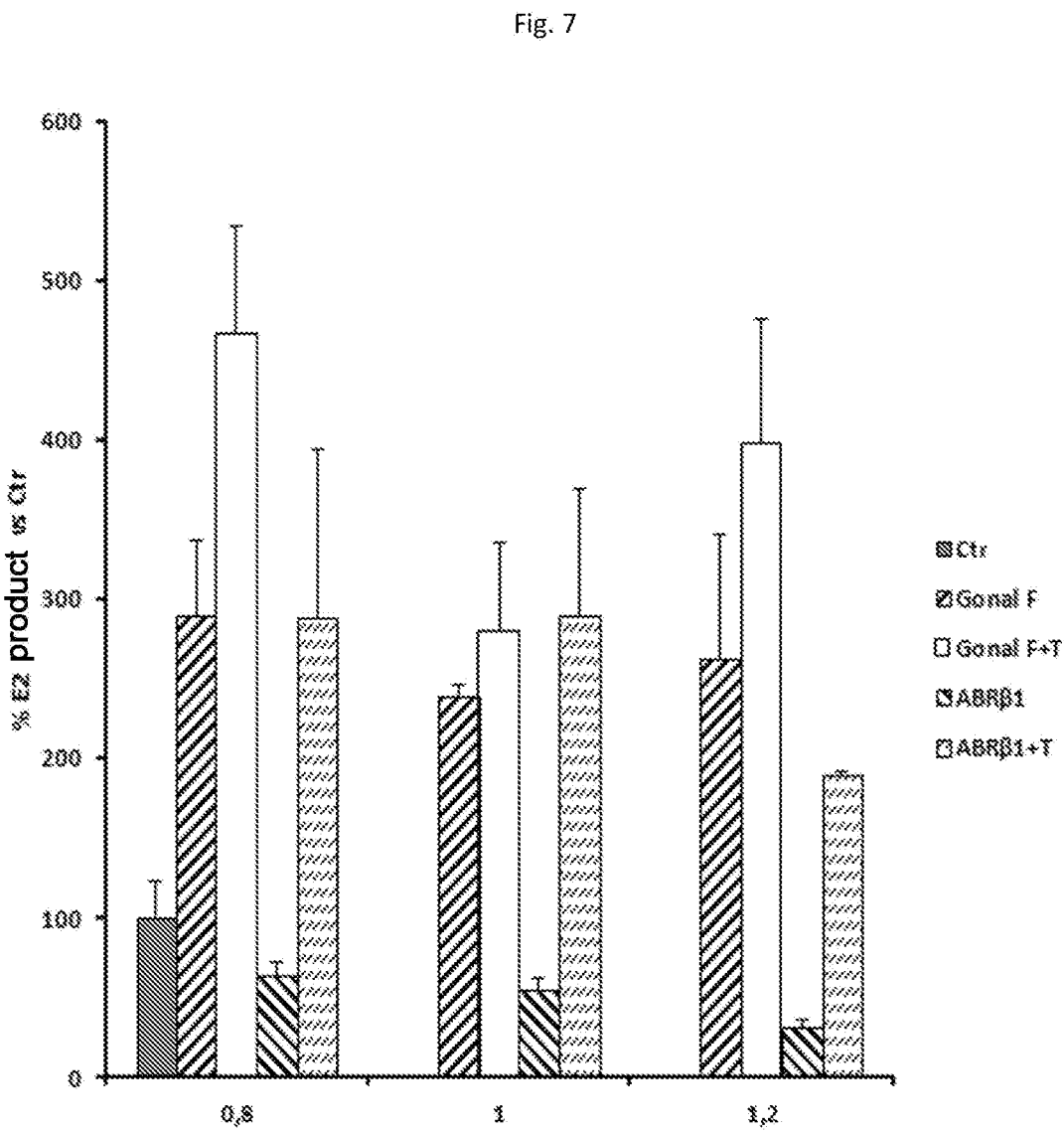
FIG. 7 shows the results of the analysis of the effect of ABRβ1 on the activation of FSHR through measurement of the production of estradiol (E2) in Sertoli cells. Data are represented as mean±SD (n=3). CTR: untreated cells; Gonal F: cells treated with the commercial drug; ABRβ1: cells treated with the purified ligand ABRβ1; T: cells supplemented with testosterone.

FIG. 7 shows the results of the analysis of the effect of ABRβ1 on the activation of FSHR through measurement of the production of estradiol (E2) in Sertoli cells. Data are represented as mean±SD (n=3). CTR: untreated cells; Gonal F: cells treated with the commercial drug; ABRβ1: cells treated with the purified ligand ABRβ1; T: cells supplemented with testosterone. The various reagents are used at concentrations shown in the figure. Gonal F binds FSHR and results in an increase of E2 by about 300% with respect to the Ctr, the ABRβ1 ligand is not capable of activating FSHR and the production of E2 is null (p≤0.0001). The treatment with testosterone reveals the maximum potential aromatase activity under different conditions (experimental control).

6. ABRβ1 Ligand Labeling and Binding to FSHR

In order to verify the hypothesis that the ABRβ1 ligand is capable of specifically and efficiently binding FSHR, it was necessary to derivatize the purified protein with fluorescent probes allowing ligand-receptor binding analyses to be carried out on cellular modelsin vitro. To this end, techniques based on fluorescence microscopy and flow cytometry were used. The ABRβ1 ligand was derivatized with two different fluorescent molecules: 4-Chloro-7-nitrobenzofurazan (NBD) and Alexa Fluor 647.

Human immortalized cell lines (ovarian cancer model), OVCAR-3, OVCAR-5, CAOV-3, were selected as in vitro modelas they express FSHR. The cells incubated for a short time with the fluorescent ABRβ1 ligand show a homogeneous and marked cell membrane decoration which correlates with the concentration of fluorescent protein used in incubation and disappears in the case of co-incubation with Gonal-F® to demonstrate the binding specificity of the ABRβ1 ligand with FSHR.

The flow cytometric analysis reveals that the percentage of labeled cells with respect to the total cells is in all cases greater than 96%.

The same results were obtained also on other cell lines. Such as LS-180 (human colon cancer model).

Figure 8:
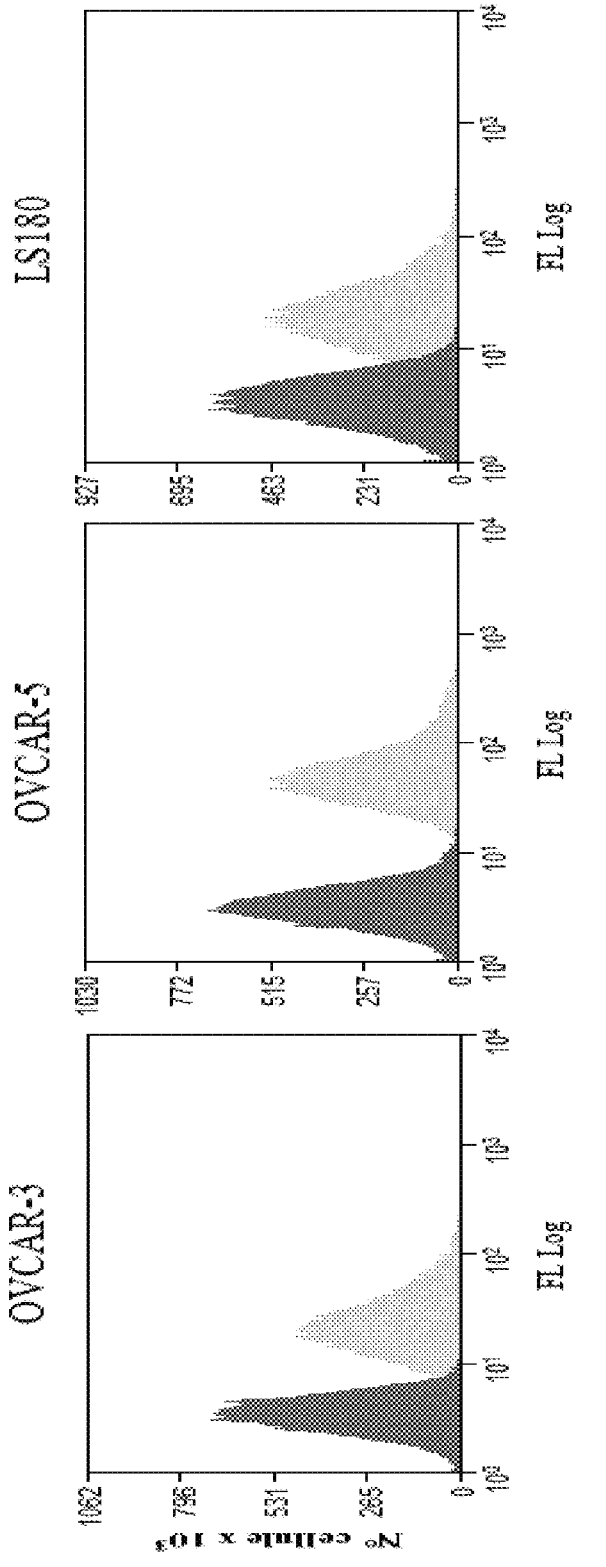
FIG. 8 shows the results of the analysis of the binding of ABRβ1 labeled with NBD to FSHR in cancer cells.

FIG. 8 shows the results of the analysis of the binding of ABRβ1 labeled with NBD to FSHR in cancer cells.

The cancer cells shown in the figure were treated with the labeled ABRβ1 ligand and then washed in saline prior to the analysis of the fluorescence signal (FL; FITC channel). The experiment was conducted using a flow cytometer. The analysis shows that cells binding ABRβ1 (light grey peak) represent more than 96% of the total cells treated (dark gray peak), (n=3).

7. Analysis of the Internalization of ABRβ1

The analysis of the effect of the ABRβ1 ligand on the internalization dynamics of the FSHR receptor were conducted by immunofluorescence and confocal microscopy. HeLa cells (cultured in complete DMEM medium) seeded on slide were transfected with the plasmid which allows the overexpression of human FSHR, 24 hours after seeding the cells were treated with 0.1 μg/ml Gonal-F®, ABRβ1 or ABRβ1 labeled with NBD.

Figure 9:
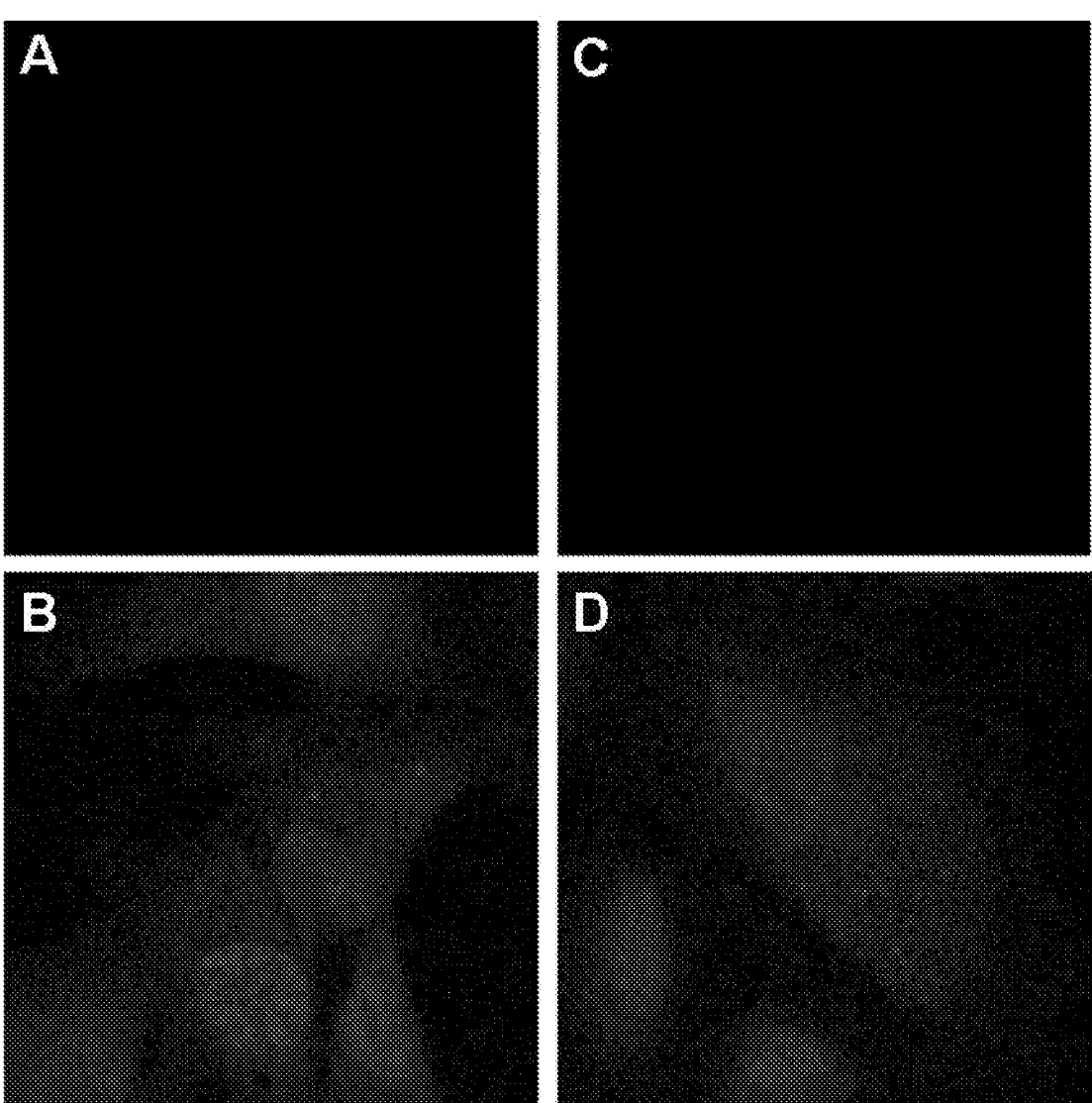
FIG. 9 shows the result of the analysis of the internalization of Gonal F (Panel A and B) and ABRβ1 (Panel C and D) in HeLa cells transformed with human FSHR. Cells incubated with FITC secondary antibody only (Panel A and C)

The cells treated with ABRβ1 labeled with NBD were fixated (as described in the materials and methods section) and analyzed in fluorescence microscopy using a confocal microscope. The cells treated with Gonal-F® or with the unlabeled ABRβ1 ligand were fixated and subjected to the immunocytochemistry protocol. In this case, the internalization of the FSHR was highlighted through the use of a specific antibody against human FSHR and a secondary antibody which allows the revelation thereof in confocal fluorescence microscopy. As shown in FIG. 9, the appearance of fluorescent cytoplasmic vesicles is observed in all cases. HeLa cells adhered on the slide were transformed with the plasmid for the expression of human FSHR. 24 hours after transfection, the cells were incubated with Gonal F or with the ABRβ1 ligand (100 ng/mL for 15 min) and then washed in saline, further incubated for 30 min at 37° C. further before being fixated and subjected to immunohistochemical analysis using a human FSHR specific antibody and a secondary conjugated with FITC which is detected by confocal fluorescence. The analysis shows that Gonal F (Panel A and B) and ABRβ1 ligand (Panel C and D) have a high rate of internalization as evidenced by the appearance of a localized signal in cytoplasmic vesicles. Cells incubated with secondary FITC antibody alone (Panel A and C).

The different techniques used reveal and confirm that the phenomenon observed is due to the specific ligand-induced internalization of the FSHR.

8. Analysis of Gonal-F®-Induced cAMP Production and ABRβ1-Induced Neutralization In order to verify the binding specificity and efficiency of the ABRβ1 ligand to FSHR, its effect on the production of cAMP (the result of the receptor binding and activation) was evaluated in competition studies with Gonal-F®. HEK293 cells were co-transfected with a plasmid containing the gene encoding for human FSHR and with a plasmid encoding for the protein probe Epac1-camps which allows to measure changes in cAMP by fluorescence microscopy. Preliminary dose-response analyses with Gonal-F® allowed to define the sensitivity, the dynamic response range of the system and the concentration at which Gonal-F® produces the greatest effect. Measures of cAMP variation in competition experiments in which the concentration of the ABRβ1 ligand is kept fixed at 500 ng/ml and the concentration of Gonal-F® is varied in the range of 1-100 ng/ml allowed to generate the competition curve Gonal-F®/ABRβ1 ligand.

Figure 10:
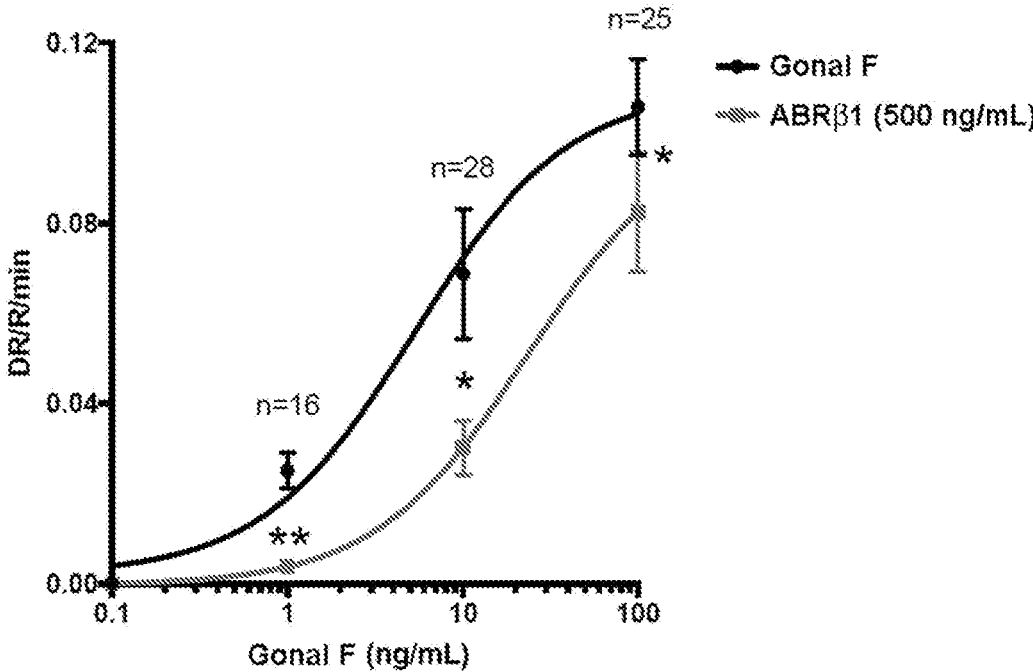
FIG. 10 shows the results of the cAMP production induced by Gonal F and neutralized by the ligand ABRβ1.

FIG. 10 shows the results of the cAMP production induced by Gonal F and neutralized by the ABRβ1 ligand. HEK293 cells were transfected with human FSHR and with the probe, which allows to measure the cytoplasmic concentration of cAMP in fluorescence by FRET (Epac2-camps). Gonal F induces the production of cAMP in a dose-dependent manner (black line). In the presence of the ABRβ1 ligand at a concentration of 500 ng/ml (grey line), the addition of 50 ng/mL Gonal F is required to obtain 50% of its maximum activity in the absence of competition. Dr/R/min, fluorescence variation normalized on the basal fluorescence. Data are represented as mean±SD (*=p≤0.01; **=p≤0.05).

The data obtained show that in the presence of 500 ng/ml of ABRβ1 ligand, 50 ng/ml of Gonal-F® are required to achieve 50% of the maximum activity of the drug in the absence of competition. Hence it follows that in order to neutralize 50 ng/ml of Gonal-F®, the most powerful FSHR ligand known, 500 ng/ml of the ABRβ1 ligand are sufficient. Such a concentration ratio, that is, 1:10, turns out to be very low and highlights the extreme effectiveness of ABRβ1 in competing with Gonal-F® for the human FSHR, also confirming the extreme affinity and specificity thereof.

9. Effect of the ABRβ1 Ligand on the Growth Rate of Cancer Cells: Competition with Gonal F Since the activation of FSHR is involved in the mechanisms which regulate cell growth, the inventors have tested the effect of the ABRβ1 ligand on the cell growth rate in three model lines of human tumor: CAOV-3, OVCAR-3 (ovarian tumor) and MDA-MB-231 (triple negative breast cancer). In all cell lines, treatment with Gonal F (0.1 μg/ml) induces at 48 hours from administration a significant increase in the rate of cell growth (CAOV-3, MDA-MB-231+40% OVCAR-3+20%). Treatment with the ABRβ1 ligand (0.1 μg/ml) reduces the rate of cell growth by 15% in CAOV-3 cells and by 40% in OVCAR-3 cells with respect to what measured in control conditions. Surprisingly, the ABRβ1 ligand in all lines is capable of canceling the effect of Gonal F on cellular growth, nullifying its effects.

FIG. 11 shows the effect of the ABRβ1 ligand on the growth of cancer cells. The cancer cells shown in figure were treated with the ABRβ1 ligand (0.1 μg/ml), Gonal F (0.1 μg/ml) or a mixture of both Gonal F+ABRβ1 (both at a concentration of 0.1 μg/ml) in a single dose at t=0 hours. Gonal F induces an increase in the growth rate, at 48 hours, by about 40% (p≤0.05) in CAOV-3 cells and MDA-MB-231 and by about 20% (p≤0.05) in OVCAR-3 with respect to the control (Ctr). The ABRβ1 ligand induces a reduction in the growth rate at 48 hours by about 15% (p≤0.1) in CAOV-3 cells and about 40% (p≤0.05) in OVCAR-3 cells. In cell lines, the ABRβ1 ligand competes with Gonal F, nullifying the effect thereof on cellular growth (p≤0.005). For clarity, S.D. (n=3) are not shown in the figure.

This means that "in vitro", the ABRβ1 ligand interacts with FSHR competing with Gonal F in comparable concentrations.

10. Effect of the ABRβ1 Ligand Labeled with Alexa Fluor 647 on the Growth Rate of Cancer Cells: Competition with Gonal F The ABRβ1 ligand was labeled with Alexa Fluor 647 so as to obtain a molecule capable of being traced in animals in "in vivo" experiments. This is important to check, for example, the specific ABRβ1 ligand accumulation within the tumor mass induced in animals. In order to verify that the labeling process does not affect the binding ability to FSHR of the ABRβ1 ligand, the experiments described in paragraph 8 were repeated. ABRβ1 Alexa Fluor 647 is capable of competing with Gonal F although in a somewhat less efficient manner with respect to the unlabeled ABRβ1 ligand (FIG. 12).

Figure 12:
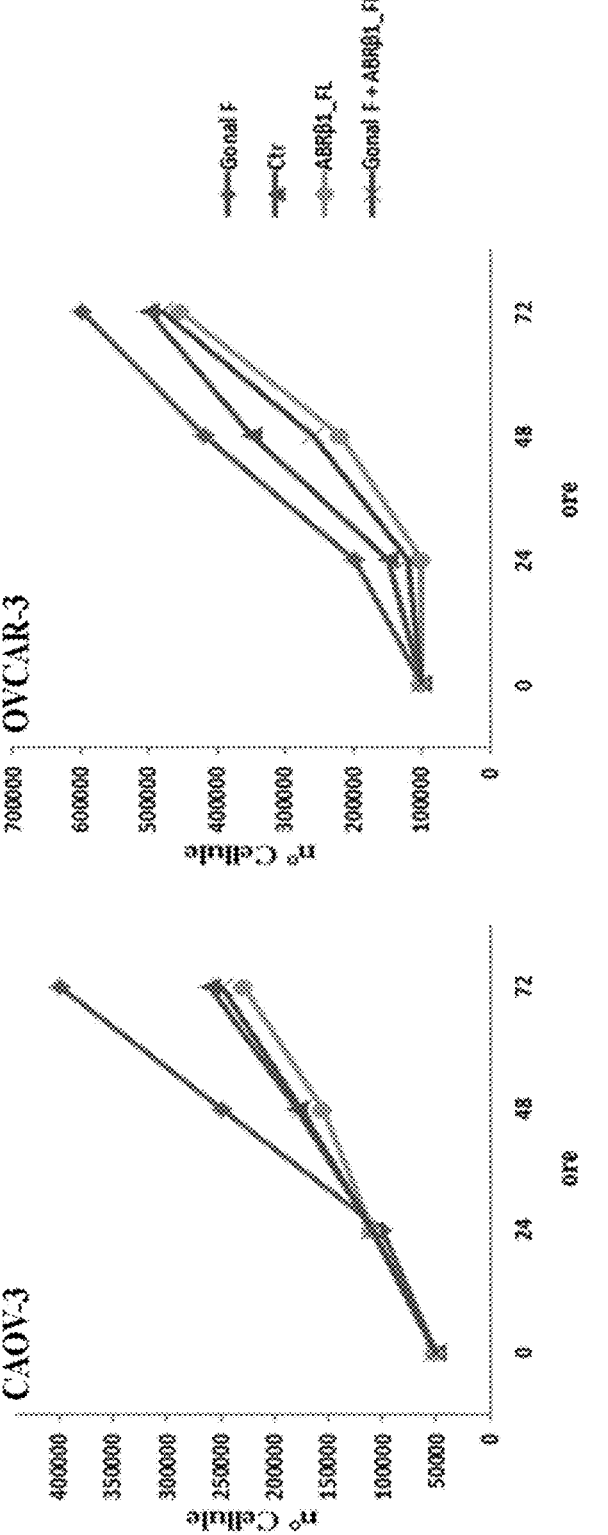
FIG. 12 shows the effect of the ligand ABRβ1 labeled with Alexa Fluor 647 on the growth of cancer cells.

In particular, FIG. 12 shows the effect of the ABRβ1 ligand labeled with Alexa Fluor 647 on the growth of cancer cells. Cancer cells were treated with the ABRβ1 ligand labeled with Alexa Fluor 647 (ABRβ1_FL) (0.1 μg/ml), Gonal F (0.1 μg/ml) or a mixture of both Gonal F+ABRβ1_FL (both at a concentration of 0.1 μg/ml) in a single dose at t=0 hours. The ABRβ1_FL ligand inhibits the effect of Gonal F in a manner similar to what is produced by the ABRβ1 ligand, proving that the Alexa Fluor 647 labeling only partially affects the effectiveness thereof. For clarity, S.D. (n=3) are not shown in the figure. The loss of efficiency is due to the binding with the fluorescent molecule which impairs the interaction ability of the ABRβ1 ligand with FSHR. The effect observed is still contained and confirms that ABRβ1 Alexa Fluor 647 can be used in "in vivo" experiments.

11. Flow Cytometric Analysis of the Internationalization of ABRβ1 NBD in OVCAR-3 and MDA-MB-231.

Cells (4×10^4 OVCAR-3 or MDA-MB-231) were seeded on 24-well plates 24 hours before the experiment. In order to identify the best experimental conditions, cells were incubated with increasing concentrations of the fluorescent ABRβ1 ligands. After 1 hour of incubation, cells were washed with the Versene solution, detached from the plates with using trypsin which is neutralized by adding 200 μL FBS. The centrifuged cells were re-suspended in Versene solution for FACS fluorescence measurements. The 488 nm laser was used for fluorophore excitation (ABRβ1 derivatized with NBD). 1×10^4 events in triplicate were analyzed for each experiment. Data analyses were performed using the FACSDiva software. As shown in FIG. 13, the internalization of the fluorescent ligand in cells depends on the concentration of fluorescent ligand used in incubation.

12. ABRβ1 Accumulates in Lysosomes Following Internalization in OVCAR-3 and MDA-MB-231.

Figure 14:
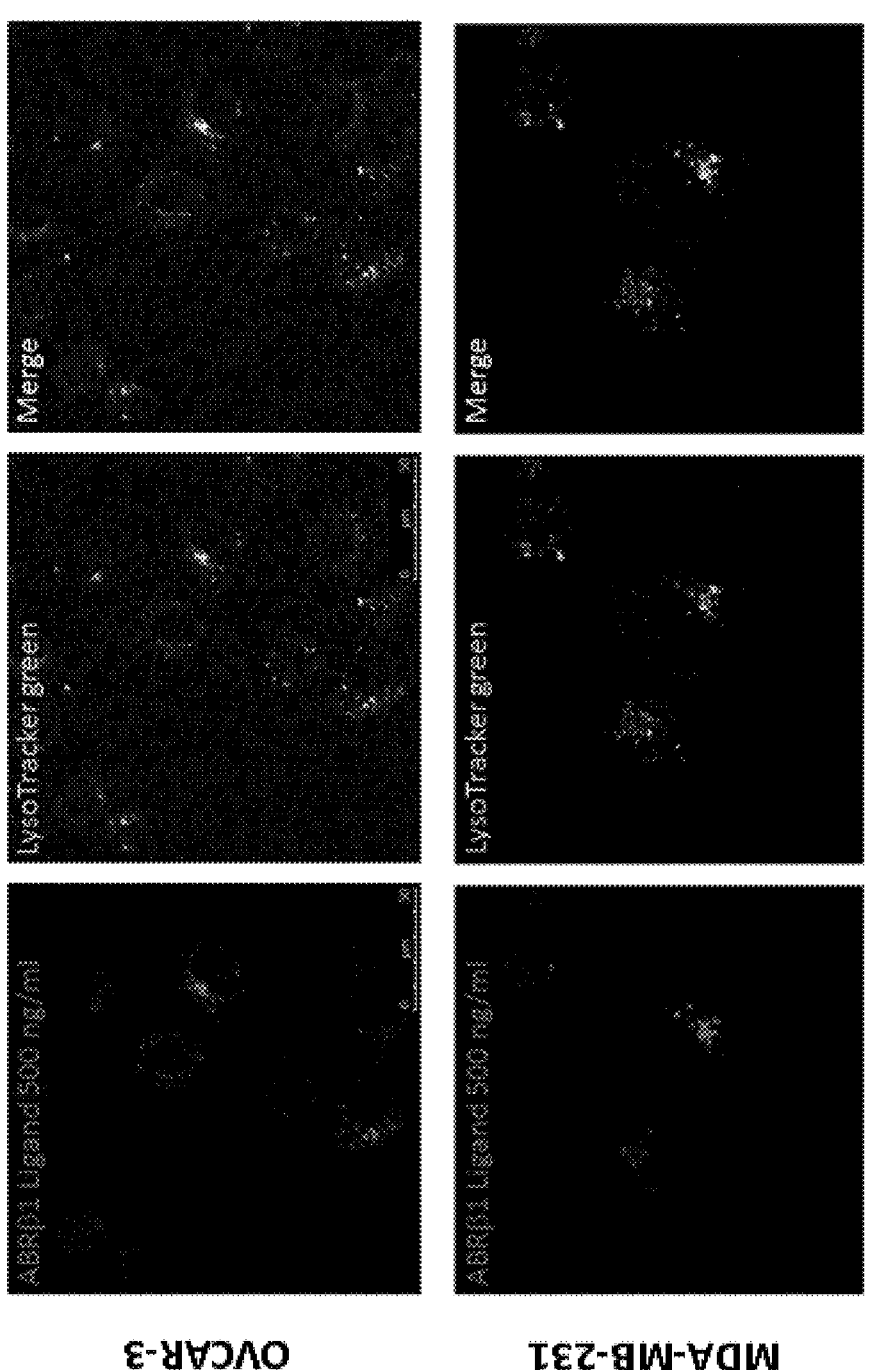
FIG. 14 shows the location of the ligand ABRβ1 and its localization in the lysosomal compartment of cancer cells.

The internalization and the subcellular localization of the ABRβ1 ligand was performed using the ligand derivatized with Alexa Fluor 647 and was evaluated through confocal microscopy on cells over-expressing the FSHR OVCAR-3 and MDA-MB-231. The cells (1×10^5 OVCAR-3 and 8×10^4 MDA-MB-231) were seeded on slides for confocal microscopy 24 hours before incubation with the fluorescent ligand. Then, the cells were co-incubated with the labeled ABRβ1 ligand (500 ng/ml ABRβ1 Alexa Fluor 647 and LysoTracker Green DND-26, 75 nM) for 1 hour at 37° C. in complete medium. Prior to the image acquisition, the cells were washed twice with HBSS solution, maintained in the same buffer and analyzed immediately by confocal microscopy. As shown in FIG. 14, in both cell lines, the signal due to LysoTracker Green, which accumulates specifically in the cell lysosomes, co-localizes with the ABRβ1 signal. This means that following the internalization, ABRβ1 is compartmentalized in the cell lysosomes.

13. Analysis of the FSHR Expression in a Panel of Tumor Cell Lines.

A panel of cell lines model of human tumors were analyzed at the FACS to verify the presence of the FSHR on the cell surface, the analysis was carried out using the specific primary antibody developed for human FSHR. Cells (0.5×10^6/sample) were harvested from the culture flasks and kept on ice in flow cytometry tubes throughout the experimental period. Three samples were prepared for each cell line: i) untreated cells, ii) cells incubated with a primary antibody against FSHR developed in rabbit (SAB4501041, Sigma-Aldrich) and with the anti-IgG secondary antibody conjugated with Alexa Fluor® 488 (TermoFisher), iii) cells incubated with secondary antibody alone. At the end of the labeling protocols, the cells are analyzed at the FACS, 2×10^5 events were acquired and analyzed for each sample using the FACSDiva software. The list of cell lines analyzed and the results are shown in FIG. 15.

14. ABRβ1 and FSHR in Infant Neuroblastoma

In order to define the FSHR gene expression pattern in infant neuroblastoma (NB), a dataset was analyzed, called "E-MTAB-16" deposited at The European Molecular Biology Laboratory EMBL).

In the database, gene expression analyses were collected, obtained using the microarray technology.

The collection consists of 504 NB samples grouped into the 7 classes listed below: risk classes, tumor evolution stages, MYCN gene state, survivors/deceased, recurrences, age at diagnosis and survival after diagnosis.

The primary data were retrieved from the database as normalized data https://www.ebi.ac.uk/arrayexpress/files/E-MTAB-161/E-MTAB-161.processed.1.zip).

The sequences identified as probes for the genes of interest were reassigned on the reference genome hg19 using the bowtie2 software.

Only the probes which identify the genes of interest with high specificity and confidence were used for subsequent analysis.

The gene expression levels obtained in the case of different probes which appear on the same gene were normalized using the median value of the available data. The analysis was carried out to delineate the FSHR gene expression in relation to many different parameters used for the classification of NB, such as patient age at diagnosis, tumor stage, the MYCN expression state.

Figure 16:
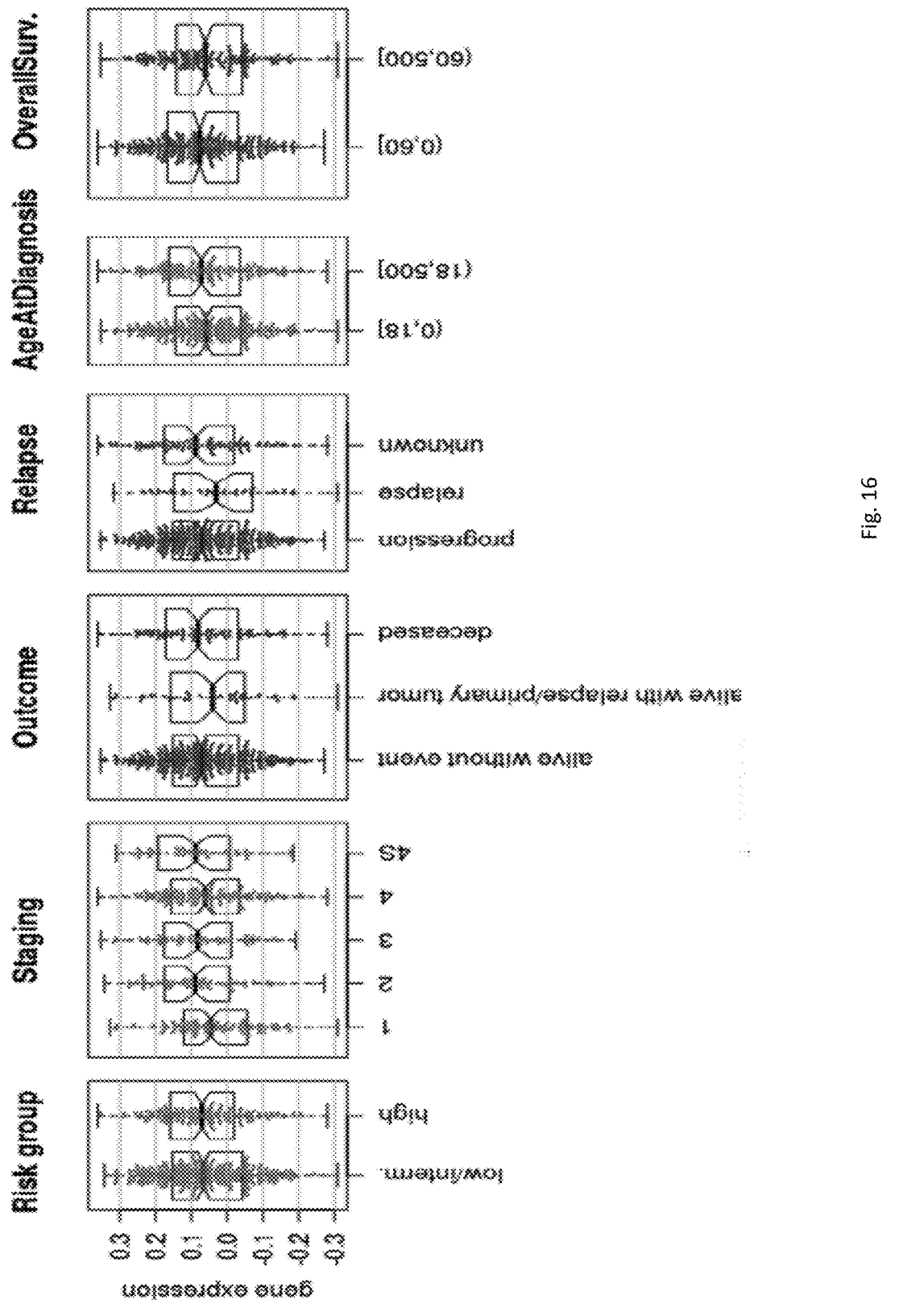
FIG. 16 shows an example of boxplots obtained as the output from the FSHR gene expression data analysis conducted by querying the ArrayExpress (EMBL) database. The dataset analyzed includes 504 human infant neuroblastoma samples.

The boxplots (FIG. 16) of the FSHR gene expression were produced and analyzed using Wilcoxon's statistical test and assigning a statistical significance value to data related to different groups.

The inventors of the present patent application found that the FSHR is overexpressed in infant neuroblastoma FSHR, in all samples forming the group of patients, regardless of the state of evolution of the pathological condition. It is relevant that FSHR is over-expressed both in samples from patients with early diagnosis and high probability of survival and in those from patients with late diagnosis and deceased.

In order to verify the expression the presence of the FSHR protein in neuroblastoma, NB3 cells were used (neuroblastoma cell model). Cells were incubated with the fluorescent ABRβ1 ligand and analyzed in fluorescence microscopy and flow cytometry.

These data show that the percentage of cells labeled with the (fluorescent) ABRβ1 ligand and which therefore express FSHR on the cell surface is higher than 96% in all cells analyzed.

Figure 17:
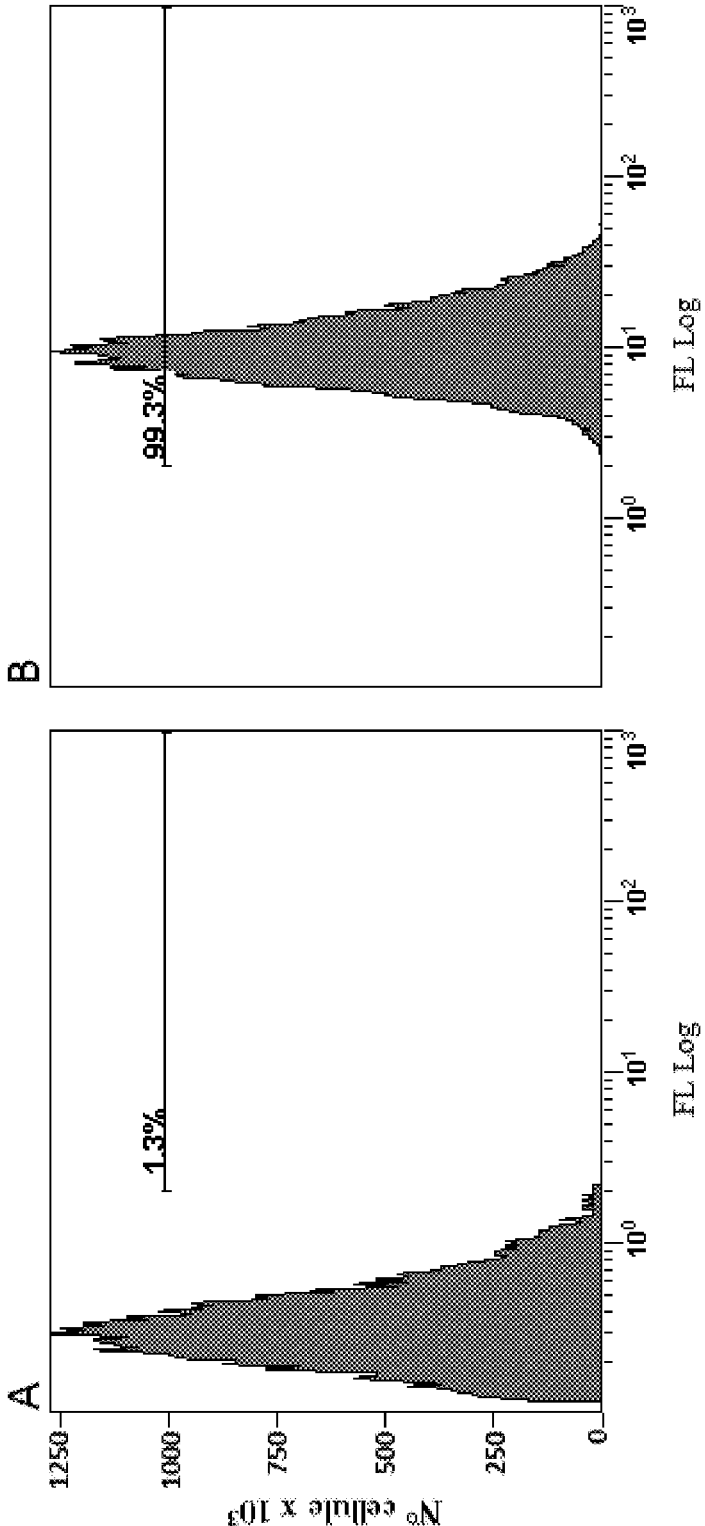
FIG. 17 shows the results of the analysis of the binding of ABRβ1 labeled with NBD to FSHR in NB3 cells.

FIG. 17 shows the results of the analysis of the binding of ABRβ1 labeled with NBD to FSHR in NB3 cells. NB3 cells (in vitro neuroblastoma model) were treated with the labeled ABRβ1 ligand and then washed in saline solution prior to analysis of the fluorescence signal (FL) conducted with flow cytometer in the FITC channel. The analysis shows that cells binding ABRβ1 (panel B) account for more than 96% of the total cells treated (Panel A), (n=3).

Moreover, microscopy experiments show that the ABRβ1 ligand, in cells NB3, has a high rate of internalization which affects the majority of cells, as demonstrated by the appearance of fluorescent cytoplasmic vesicles in more than 96% of cells analyzed.

Figure 20:
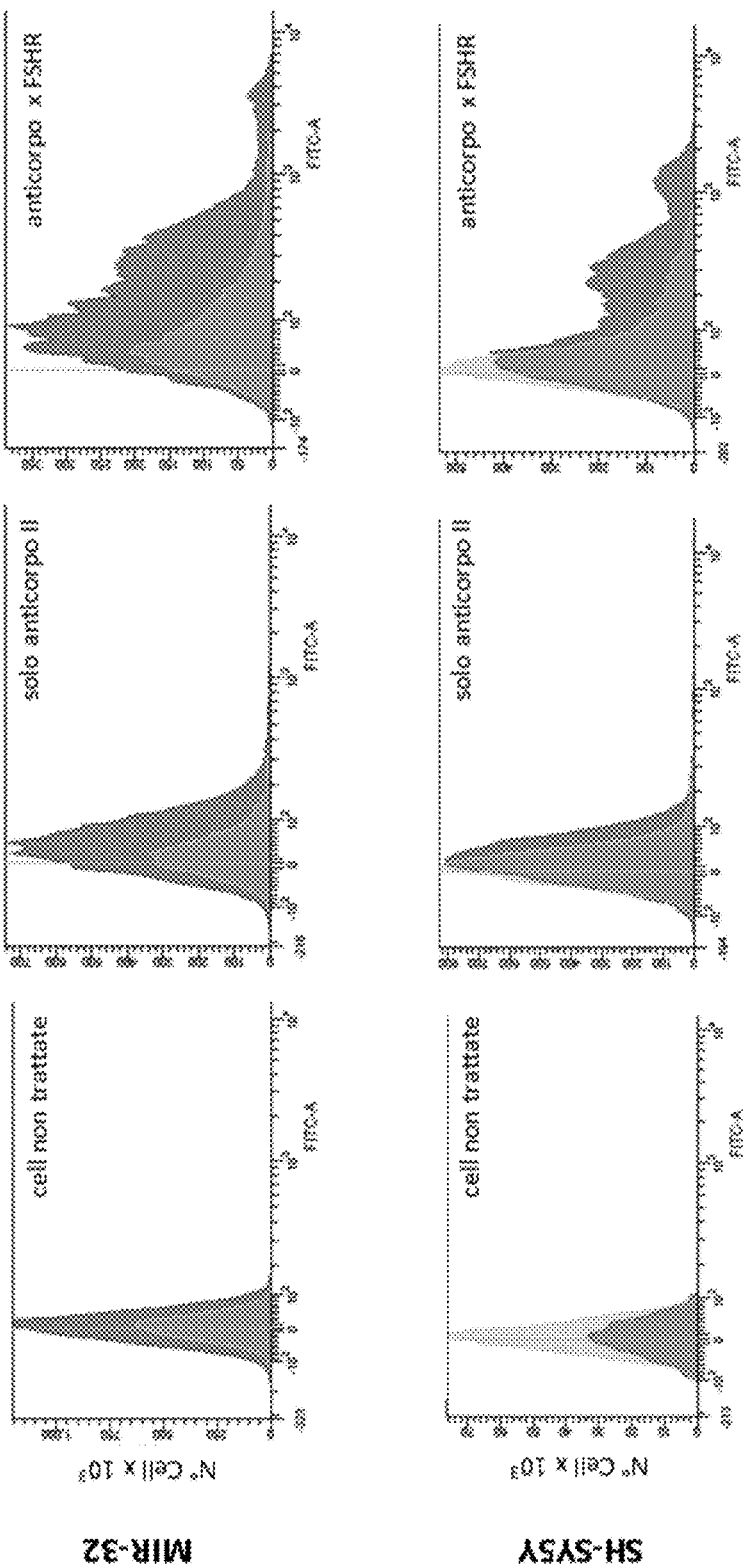
FIG. 20 shows the expression analysis of FSHR by immunoflow cytometry technique in human neuroblastoma cancer cells.

FIG. 18 shows the results of the internalization of ABRβ1 labeled with NBD in NB3 cells. The NB3 cells adhered on a slide were incubated with the labeled ABRβ1 ligand (150 ng/ml for 15 min) and then washed in saline, incubated again for 30 min at 37° C. prior to the fluorescence microscopy analysis (FITC channel). The analysis shows that the ABRβ1 ligand has a high rate of internalization. A fraction higher than 96% of treated cells shows the appearance of signal localized in cytoplasmic vesicles (panel B) (n=3). Untreated cells (Panel A). The flow cytometric analysis using the specific antibody against human FSHR on human neuroblastoma model cells IMR-32 and SH-SY5Y reveals the presence of the receptor on the cell membrane, FIG. 20.

15. Preliminary Analysis of Acute Toxicity of the ABRβ1 Ligand

In a preliminary study, the acute toxicity of the ABRβ1 ligandin vivo was assessed. To this end, CD1 strain male mice (n=3) and female mice (n=3) aged 12-14 weeks were treated with the ABRβ1 ligand (carrier: 140 mM NaCl, 50 mM NaHPO$_4$, 60 μM Tween 20, pH 6.8). Each mouse was treated with 200 μl/25 g of solution containing ABRβ1 at a concentration of 1.25 mg/ml pre-filtered on a 0.22 μm PES membrane. 50 μl of the solution were plated on LB/Peptone/Agar and incubated at 37° C. for 3 days (C.F.U.=0) and the endotoxin content was determined (E.U.<0.1/1 μg ABRβ1). Control mice are represented by untreated animals (n=2) or animals treated with carrier alone (n=2). The animals were weighed prior to treatment, at 24 hours and then every 72 hours up to 15 days after I.V. injection, the behavior was observed for 2 hours after treatment and at each subsequent weighing operation, which is carried out in the morning between 9:00 and 10:00.

Figure 21:
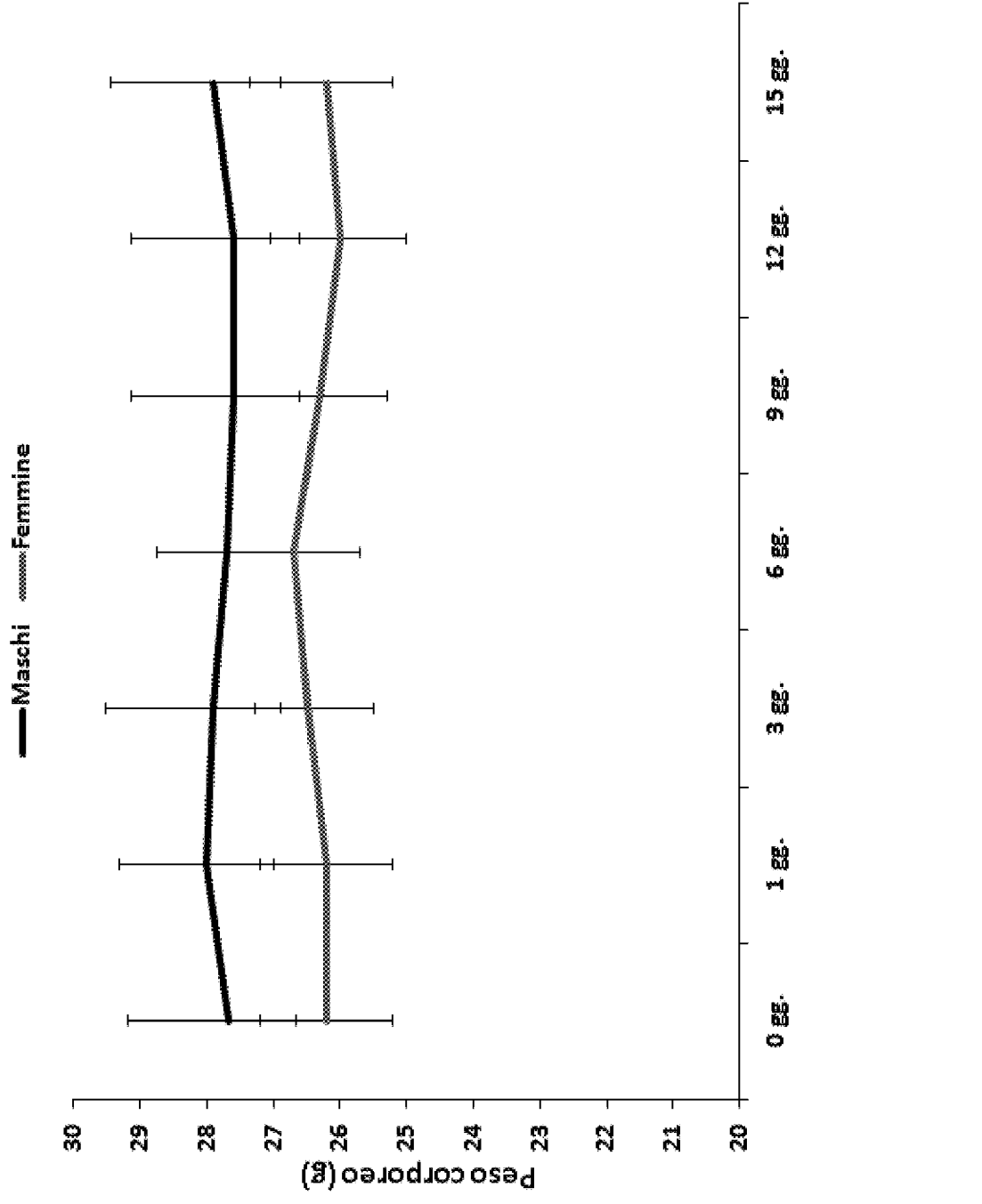
FIG. 21 shows the effect (over time) of the caudal vein injection of ABRβ1 in a mouse model.

The animals treated with carrier alone show no sign of pain at the time of treatment and in the following 2 hours. The behavioral observation over the next 15 days does not show the appearance of anomalies or signs of distress. No pain was observed in any of the mice treated with the ABRβ1 ligand (10 mg/kg) over 2 hours or in the 15 days following treatment. The body weight remains, over 15 days, in all cases, consistent with that measured before treatment (FIG. 21), showing no significant differences between the different groups of animals of the same sex.

Mice were sacrificed at 15 days after treatment and the condition of the major organs was assessed macroscopically. In all organs observed (thymus gland, heart, lungs, stomach, liver, spleen, intestine, kidneys, adrenal glands, ovaries, testes), no significant macroscopic changes (with respect to the controls) due to treatment with carrier or with ABRβ1 (10 mg/kg) were observed.

Materials and Methods

Construction of the Vector

For the transformation of bacteria and plant cells, we used the pABR vector derived from the binary vector pGreenII in which the polycloning site and the lacZ gene sequence was removed and substituted with a new sequence containing the gene which confers kanamycin resistance in eukaryotes and a new expression cassette.

The expression cassette is formed by the promoter of the gene transcription of the duplicate Cauliflower mosaic virus CaMV 35Sx2 (Franck et al. 1980) downstream of which the TEV sequence that boosts both the transcription and the translation of the gene encoding for the human protein was inserted (Nopo et al. 2012).

Between the VTE sequence and the nopaline synthase terminator (Luo Z. et al. 2007), which serves to improve the stability of the mRNA produced and the efficiency in terminating its translation, is the polycloning site for inserting the cNDA sequence encoding for the exogenous protein (FIG. 1, in which RB/LB: recombinant-specific sites, left and right border; Tml p: tumor morphology large DNA promoter; NPT II: neomycin phosphotransferase II; Tml t: tumor morphology large DNA terminator; CaMV35 x2_p: cauliflower mosaic virus promoter; TEV 5': untranslated TEV, 5' sequence; Nos t: nopaline synthase terminator).

Construction of the Sequence Encoding for the ABRβ1 Ligand (Human FSHβ)

The amino acid sequence of human FSHβ was derived by querying the UniProtKB database available at <www.expasy.org>. The protein identification number is P01225.

The sequence of the mature protein was suitably modified for the purposes of the present invention, obtaining the new amino acid sequence shown below:

| | |
|---|---|
| SEQ ID NO: 2 | HHHHHHNSCELTNITIAIEKEECRFCISINTTWCAGYCYT RDLVYKDPARPKIQKTCTFKELVYETVRVPGCAHHADSLY TYPVATQCHCGKCDSDSTDCTVRGLGPSYCSFGEMKEKDE L |

Through the use of bioinformatics tools, the nucleotide sequence encoding for such a protein was created, then such a sequence was optimized for expression in plant cells.

At 5' and 3' of such a sequence are the recognition sites for the restriction enzymes Eco RI and Xba I for the correct cloning inside the expression cassette in the pABR vector.

The DNA fragment corresponding to such a sequence was obtained through a gene synthesis process in the laboratory.

The new sequence encoding for the ABRβ1 ligand, including the signal peptide directing to the endoplasmic reticulum, is shown below.

| | |
|---|---|
| SEQ ID NO: 3 | GAATTCAACAATGGCTACTCAGAGAAGGGCTAACCCATCTT CTCTTCACCTGATTACCGTGTTCTCTCTGCTTGTGGCTGTG GTGTCTGCTGAGGTGTTCCATCATCACCATCATCACAATTC TTGCGAGCTGACCAACATCACCATTGCTATCGAGAAAGAAG AGTGCAGGTTCTGCATCAGCATCAACACTACTTGGTGCGCT GGTTACTGCTACACCAGGGATCTTGTGTACAAGGATCCTGC TAGGCCTAAGATCCAAAAGACCTGCACCTTCAAAGAGCTGG TTTACGAGACTGTTAGGGTGCCAGGTTGTGCTCATCATGCT GATTCTCTGTACACCTACCCTGTTGCTACTCAGTGCCATTG CGGTAAGTGCGATAGCGATTCTACTGATTGCACCGTGAGAG GTCTGGGACCTTCTTACTGTTCTTTCGGTGAGATGAAAGAA AAGGATGAGCTGTAGTCTAGA |

Cell Culture in Suspension of *Nicotiana benthamiana*

The cell culture of *Nicotiana benthamiana* is maintained in a 250 ml volume of liquid MS medium (Murashige 1962), 30 g/L sucrose and 2 mg/L naphthalene-acetic acid (NAA) and 0.2 mg/L kinetin.

Sub-cultures are prepared every 7 days by transferring an aliquot of 125 ml of cell suspension in the fresh medium.

The cells are incubated under stirring (120 rpm) in the dark and at a constant temperature of 25° C.

Stable Transformation of the *Nicotiana benthamiana* Cell Culture

The *Agrobacterium tumefaciens* (LBA4404) transformed with the pABR plasmid was cultured in the YEP medium (0.5% w/v yeast extract, 0.5% w/v plant peptone, 25 g/L LB-Broth Miller) supplemented with 100 mg/L of streptomycin and 50 mg/L of kanamycin (Duchefa).

A 25 ml bacterial culture was prepared in a 100 ml flask incubated at 28° C., 120 rpm up to reaching 1 OD.

The bacteria were then harvested by centrifugation (10 min at 4000 g at RT) and resuspended in 25 ml MS. 200 µl of the bacterial suspension are inoculated in 25 ml of *Nicotiana benthamiana* culture (fresh weight of plant cells equal to 9 g).

After 48 hours in co-culture in the dark, 25° C. and 120 rpm, the cells were filtered using a nylon mesh, washed with an excess of culture medium and then resuspended in 25 ml of the same medium. The cells were then seeded onto Petri dishes containing the selection medium consisting of MS supplemented with 0.9% w/v agar, 250 mg/L carbenicillin and 100 mg/L kanamycin (Duchefa).

The capsules were incubated at 25° C. in the dark for about 3 weeks, up to the appearance of calluses. Subsequently, the calluses are transferred into fresh selection medium every 15 days for 2 months. After this period, the stable clones are maintained in MS without antibiotics.

Purification Protocol of the ABRβ1 Ligand from Cellular Culture in Suspension of *Nicotiana benthamiana*

1. Preparation of the Extraction Buffer

Extraction buffer: 50 mM $Na_2HPO_4$, 150 mM NaCl, 20 mM citric acid, 40 mM ascorbic acid, 5 mM EDTA, 1 mM PMSF, 0.05% (v/v) Tween-20, pH 6.5 supplemented with 1% (w/v) XAD-4 and 1% (w/v) polyvinylpolypyrrolidone (PVPP).

Polystyrene resin XAD-4 requires treatment before being added to the extraction buffer, which consists of a wash in methanol for at least 1 or 2 h followed by an abundant rinsing with deionized water.

PVPP must be added to the extraction buffer at least 2-4 hours before use, in order to allow hydration thereof.

2. Extraction

An aliquot of cells in suspension, filtered on braid (cut-off of about 50 µm) and stored at −80° C. is placed at 4° C. and thawed overnight. Buffer 20 mM $Na_2HPO_4$, 10 mM EDTA, pH 7.2 is added in a ratio of 2:1, i.e. 2 ml buffer per gram of cells. The suspension is maintained at 4° C. under constant stirring for 1 hour and then centrifuged at 18000 rpm for 20 min at a controlled temperature of 4° C., discarding the supernatant.

The extraction buffer is added to the pellet in a ratio of 3:1 (3 ml/gram cell) and maintained at 4° C. for 1 h. The extract is then centrifuged at 18000 rpm for 20 min at a temperature of 4° C., recovering the supernatant.

3. Precipitation with Ammonium Sulfate

Ammonium sulfate is added to the extract up to obtain a 70% saturation concentration (concentration at which the complete precipitation of the ABRβ1 ligand was demonstrated).

The solution is kept at a temperature of 4° C. for 1 h under constant stirring. After centrifugation at 18000 rpm for 20 min at 4° C., the supernatant is discarded and the precipitate resuspended in $\frac{1}{10}$ of the initial volume in a buffer suitable for promoting the interaction between the proteins and the IMAC resin.

4. IMAC Chromatography

The precipitate obtained after treatment with ammonium sulfate is resuspended in $\frac{1}{10}$ of the initial volume in a buffer 20 mM $Na_2HPO_4$, 300 mM NaCl, 10 mM imidazol, pH 8.0, centrifuged at 18000 rpm and filtered at 0.22 μm. The resulting solution is loaded to a column packed with Ni Sepharose 6 FF resin (GE Healthcare, 17-5318-01) balanced with a buffer 20 mM $Na_2HPO_4$, 300 mM NaCl, 10 mM imidazole, pH 8.0 and eluted with a buffer 20 mM $Na_2HPO_4$, 300 mM NaCl, 500 mM imidazole, pH 8.0 using a multiple step gradient. Absorbance is monitored at 280 and 254 nm. Fractions harvested by SDS-PAGE electrophoresis and immunoblotting techniques using Enhanced ChemiLuminescence (ECL) as detection technique.

These analyses use an anti-hFSHβ polyclonal primary antibody expressed in rabbit (Abcam, AB171431), a secondary IgG anti-rabbit antibody derivatized with horseradish peroxidase (KPL, 474-1506) and human recombinant hFSH-β expressed in *E. coli* as the reference standard (Abnova, H00002488-Q01).

5. Size-Exclusion Chromatography

Fractions derived from IMAC chromatography in which the ABRβ1 ligand was found are combined and loaded onto a column packed with Sephadex G-25 Medium resin (GE Healthcare, 17-0033-01). The column is balanced and eluted with a buffer of 50 mM sodium acetate, 150 mM NaCl, 60 μM Tween-20, pH 5.5. Absorbance is monitored at 280 and 254 nm.

The eluate harvested at the chromatographic peaks is analyzed by SDS-PAGE electrophoresis and immunoblotting techniques with ECL detection in order to monitor the presence of the recombinant protein therein. These analyses use an anti-hFSHβ polyclonal primary antibody expressed in rabbit (Abcam, AB171431), a secondary IgG anti-rabbit antibody derivatized with horseradish peroxidase (KPL, 474-1506) and human recombinant hFSH-β expressed in *E. coli* as the reference standard (Abnova, H00002488-Q01).

6. Ion Exchange Chromatography

Fractions derived from molecular exclusion chromatography found to be positive to the presence of the ABβR ligand are combined and loaded on a column packed with SP Sepharose HP resin (GE Healthcare, 17-1087-01) balanced with a buffer 50 mM sodium acetate, 150 mM NaCl, 60 μM Tween-20, pH 5.5 and eluted with a buffer 50 mM sodium acetate, 1 M NaCl, 60 μM Tween-20, pH 5.5 using a multiple step gradient. Absorbance is monitored at 280 and 254 nm. As with the previous chromatographies, it is necessary to analyze the harvested fractions in order to determine in which of them there is the presence of the human recombinant protein.

Deglycosylation Through PNGase F

An aliquot of ABRβ1 ligand from ion-exchange chromatography was concentrated to 0.5 mg/ml using a Vivaspin with a cut-off of about 10 kDa (VS0403, Sartorious) and replacing the buffer with a buffer 50 mM $NH_4HCO_3$, 0.1% (v/v) Rapigest SF (Waters, Manchester, U.K.) pH 7.9.

The protein concentration was determined by bicinconinic acid assay (QuantiPro™ BCA Assay Kit, QPBCA, Sigma Aldrich) using the protocol described by the manufacturer. The sample supplemented with PNGase F (Roche Custom Biotech, Mannheim, Germany) in a molar ratio of 1:50 (enzyme:substrate) was incubated overnight at a constant temperature of 37° C.

At the end of the reaction, the solution was supplemented with 45 trifluoracetic acid (w/v) and centrifuged at 13,000 rpm for 10 min.

The sample was then analyzed by SDS-PAGE (Laemmli 1970) on 12% polyacrylamide gel and high performance mass spectrometry.

In Situ Tryptic Digestion

The polyacrylamide gel stained with Coomassie Brilliant BlueG250 is rinsed with ultrapure water and the electrophoretic band corresponding to the protein to be sequences is incised. The band is cut into small fragments which are washed with 100-150 μl of ultrapure water for 5 minutes. It is centrifuged and the liquid is eliminated. A volume of acetonitrile ($CH_3CN$) is added, equal to 3-4 times the volume of the fragments and waiting 10-15 minutes, up to have a "creased" shrinking of the cubes.

The supernatant is removed and brought to dryness by means of a freeze dryer. It is recovered with buffer of 0.1 M $NH_4HCO_3$, 10 mM DTT up to cover the fragments and incubated for 30 minutes at 56° C. to reduce the disulfide bonds of proteins.

It is centrifuged, the liquid is removed and it is treated again with acetonitrile as noted above.

Acetonitrile is replaced with buffer of 0.1 M $NH_4HCO_3$, 55 mM iodoacetamide and it is incubated protected from light for 20 minutes at room temperature, so as to derivatize the cysteine residues.

The iodoacetamide solution is removed and it is washed with about 150 μl of buffer of 0.1 M $NH_4HCO_3$ for 15 minutes.

It is centrifuged, the liquid is removed and it is treated again with acetonitrile.

If the gel fragments still have a blue staining, they are rehydrated with 150 μl of buffer of 0.1 M $NH_4HCO_3$ for 10-15 minutes.

Then, an equal volume of acetonitrile is added and kept on an orbital shaker for 20 minutes.

It is centrifuged, the solution is removed and it is treated with acetonitrile, bringing to dryness with a freeze drier.

These steps are repeated until the blue staining persists.

Subsequently, 13 μl of a solution of 12.5 ng/μl of a trypsin modified solution are added (Sequencing Grade Modified Trypsin V5111, Promega) and the fragments are covered with μg 50 mM $NH_4HCO_3$.

The samples are kept at 4° C. for about 30-45 minutes to allow fragments to rehydrate and absorb the solution containing the enzyme.

During this step, it is checked whether the volume of the solution is sufficient to cover the fragments and buffer 50 mM $NH_4HCO_3$ is optionally added. The samples are left incubated for 24 h at a controlled temperature of 37° C.

At the end of the incubation, the peptides derived from the tryptic proteolysis are extracted.

1) 10-15 μl of buffer 25 mM $NH_4HCO_3$ are added to the solution and the samples are stirred at 37° C. for 15 minutes using a thermomixer. It is centrifuged and a volume of $CH_3CN$ equal to 1-2 times that of the gel fragments is added. It is stirred for 15 minutes at 37° C. in a thermomixer. It is centrifuged and the supernatant is collected.

2) The residual gel fragments are admixed with 40-50 μl of formic acid (HCOOH) at 5% (v/v). The samples are kept under constant stirring at 37° C. for 15 minutes. It is centrifuged and a volume of $CH_3CN$ equal to 1-2 times that of the gel fragments is added. It is stirred for 15 minutes at 37° C. in a thermomixer. It is centrifuged and the supernatant is collected.

The extracts are combined and evaporated to dryness in a lyophilizer.

Chromatographic Analysis of the Tryptic Digest

Following proteolysis in situ, the protein material was lyophilized and resuspended in formic acid:acetonitrile: water 2:3:95.

20 µl were loaded onto a Vydac C18 column (1×150 mm, 5 µm particle size, 300 A porosity) balanced with a 2% (v/v) aqueous solution acetonitrile, 2% (v/v) formic acid. The column is eluted at 50 µl/min with a linear gradient of acetonitrile 3-65% over 25 minutes.

The eluate was examined by monitoring the Total Ion Current (TIC) using a mass spectrometer Xevo G2-XS Q-TOF.

Determination of the Aggregation Percentage by Molecular Exclusion Chromatography The standard aggregation state of the ABRβ1 ligand was evaluated by molecular exclusion chromatography using a YARRA column, 3 mm SEC 3000, 150 mm×7.8 mm (Phenomenex) with partition interval of 10-600 kDa.

20 µl of an aliquot of ABRβ1 ligand (160 µg/ml) were loaded and the column was eluted with a buffer of 20 mM $Na_2HPO_4$, 150 mM NaCl, pH 7.4.

Stability Analysis by Fluorimetric Technique

An aliquot of ABRβ1 (250 µl of purified protein) was diluted to a final volume of 1600 µl (final concentration of ABRβ1 equal to 1 µM with buffer of 20 mM HEPES pH 7.4, 0.15M NaCl, 0.1% PEG-8000 (w/v). The sample was analyzed (T0) and then stored at 4 C for one week. The analysis was repeated at intervals of 24 hours on the same sample. The fluorescence spectrum was performed under the following conditions: T=25° C., $\lambda_{exo}$=280 nm, $\Box\lambda_{em}$=295-500 nm.

Assigning the Sulfide Bonds

An aliquot of ABRβ1 ligand was subjected to enzymatic deglycosylation through PNGase F as described above and the reaction mixture was analyzed by polyacrylamide gel electrophoresis in non-reducing conditions. The gel was stained with Coumassie Brilliant Blue G250. The band corresponding to the ABRβ1 ligand completely deglycosylated was subjected to triplicate digestion in situ as described above, but keeping the sulfide bonds intact and thus avoiding the reduction and alkylation of the cysteine residues.

The freeze-dried product of the peptide mixture derived from tryptic proteolysis was recovered in a buffer of 50 mM $NH_4HCO_3$, 1 mM $CaCl_2$, pH 8.2 supplemented with subtilisin (Subtilisin Carlsberg P-5380, Sigma) in a molar ratio enzyme:substrate equal to 1:50.

The solution was left incubated at the controlled temperature of 37° C. overnight and then lyophilized.

The sample was solubilized again in formic acid:acetonitrile:water 2:3:95.

A volume equal to 20 µl was loaded onto a Vydac C18 column (1×150 mm, 5 µm particle size, 300 A porosity). The column was eluted at a constant flow of 50 µl/min with a linear gradient of acetonitrile from 3% to 65% over 12 minutes. The analysis was monitored by recording the TIC (Total Ion Current) signal using a mass spectrometer Xevo G2-XS Q-TOF and the molecular weight of the species present was determined for each chromatographic peak.

Isolation and Cultures of Sertoli Cells

Testicles of piglets from prepubescent male animals, Large-White breed aged 7-15 days were used for the preparation of Sertoli cells (SC). The material was collected and stored properly by qualified personnel during the routine operations of castration relating to breeding, therefore the use thereof in in vitro experiments for research purposes did not require the approval by the local Ethics Committee.

The SC isolation procedure involves the removal of the testes from anesthetized piglets. After removal of the fibrous cap, the testicles were finely shredded to obtain a homogeneous tissue fragmentation which was subsequently subjected to sequential enzymatic digestions using 2 mg/ml collagenase P (Roche Diagnostics) in Hanks balanced saline (HBSS, Sigma-Aldrich).

The digestion continues up to the physical breakdown of the seminiferous tubules.

After washing, the suspension of broken down tissue was incubated with the HBSS solution supplemented with trypsin and DNase I for 15 min (Sigma-Aldrich).

At the end of this second digestion, the pellet of tissue obtained after decanting was washed twice in HBSS and then centrifuged at 120 rpm for 3 min. The resulting pellet was filtered through a stainless steel 500 micrometer mesh and resuspended in a buffer consisting of 2 M glycine, 2 mM EDTA, pH 7.2. The purpose is to eliminate all the residual Leydig cells.

The residual tubules without peritubular cells were then harvested and maintained in culture in the presence of 0.166 nM retinoic acid (Sigma-Aldrich) and 5 ml/500 ml of insulin/selenium (Becton Dickinson). The cell culture is set up in an incubator at 37° C. After 3 days of culture, cells were treated so as to eliminate any residual germ cells (Galdieri et al. 1981; Korbutt et al. 1997; Luca et al. 2005; Luca et al. 2007).

Measurement of the Aromatase Enzyme Activity

Before proceeding with the various hormone treatments, the viability of cultured cells was evaluated by staining with ethidium bromide and fluorescein diacetate (Sigma-Aldrich) in fluorescence microscopy (Nikon Optiphot-2, Nikon Corporation). In order to evaluate the activity of α-aromatase, $20\times10^6$ were treated for 3 days with different concentrations of the follicle stimulating hormone (Gonal-F) or with the same concentrations of ABRβ1 ligand; at the end of the treatment period, 0.2 mg/ml testosterone were added to the cultures and incubated for additional 8 hours.

At the end of the stimulation, 17β-estradiol (E2) produced is released in the cell culture medium and it was evaluated using a specific high-sensitivity kit (ADVIA Centaur, Estradiol-6 III, Bayer Diagnostics).

ABRβ1 Ligand Labeling with Fluorescent Molecules

For in vitro binding and in vivo localization experiments, the ABRβ1 ligand was conjugated with two different fluorescent molecules: 4-Chloro-7-nitrobenzofurazan (NBD) (Sigma) and Alexa Fluor 647 (Thermo Fisher Scientific).

For the NBD labeling, a concentrated solution of 50 mM in acetonitrile of the fluorescent probe was prepared.

The labeling reaction of the ABRβ1 ligand 50 µM/ml occurs in solution, 50 mM sodium acetate, 500 mM NaCl, 60 µM Tween 20, 1 mM ethylenediaminetetraacetic acid (EDTA), 30 mM tris(hydroxymethyl)aminomethane (Tris/HCl) pH 7.0 and 5 mM NBD (Bernal-Perez et al. 2012).

The solution is incubated at 24° C. for 16 hours, the labeling of the protein and the possible presence of aggregation are evaluated through fluorometer and fluorescence microscope analysis (exc. 465 nm; em. 515 nm). As for the conjugation of the ABRβ1 ligand with Alexa Fluor 647 (exc. 650 nm; em. 665 nm), the commercial kit Alexa Fluor 647 Antibody Labeling Kit (Thermo Fisher Scientific) was used, following the instructions provided by the manufacturer.

Analysis of the Binding to the ABRβ1 Ligand Receptor by Flow Cytometry

Stabilized human cell lines (OVCAR-3, OVCAR-5 of ovarian cancer and LS180 of colon carcinoma) and the primary ovarian carcinoma line A116 were cultured in RPMI1640 medium supplemented with 10% heat-inactivated fetal bovine serum, 1% glutamine and 1% penicillin streptomycin. Some control experiments were conducted in the absence of antibiotics or after 24 hours of culture in serum-free medium to exclude any interference by serum components or by antibiotics.

The cells upon immunofluorescence assay were detached from the culture support through incubation with trypsin-EDTA and after being counted, they were diluted to a concentration of 100,000 cells/100 μl and incubated with the fluorescent ABRβ1 ligand. Direct immunofluorescence using cytofluorimetric analysis was conducted on cells pre-incubated for 15 min at 37° C. with 10 μl/ml (350 ng) ABRβ1 ligand labeled with NBD, the analysis was carried out using the FITC channel at the flow cytometer. The cell labeling can also be highlighted at lower concentrations of the ABRβ1 ligand, the fluorescence signal is no longer noticeable when the cells are preincubated with ABRβ1 ligand concentrations lower than 70 ng/ml. Before the flow cytometry analysis, in order to assess the cell viability and the binding of the ABRβ1 ligand without intervention of proteolytic enzymes which could alter the results by causing the detachment of the ligand from the specific receptor, some experiments were conducted without detaching the cells from the substrate, such analyses were conducted using a confocal microscope Olympus FV500.

ABRβ1 Internalization

The analysis of the effect of the ABRβ1 ligand on the internalization dynamics of the FSHR receptor were conducted by immunofluorescence and confocal microscopy. HeLa cells (cultured in complete DMEM medium) seeded on slide were transfected with the plasmid which allows the overexpression of human FSHR, 24 hours after seeding the cells were treated with 0.1 μg/ml Gonal-F®, ABRβ1 or ABRβ1 labeled with NBD.

The cells are then fixated in 4% paraformaldehyde (w:v PBS1×, Phosphate-buffered saline) for 30 minutes at 4° C. and washed in PBS 1× (3 washes of 5 minutes each). In case of immunofluorescence, the fixated cells are permeabilized by incubation with PBS 1×, supplemented with 1% BSA (bovine serum albumin) and 0.1% Triton-X100 (Sigma) for 5 min. at room temperature. The permeabilization solution is eliminated by washing with PBS 1× (3 washes of 5 min. each). The cells are then incubated with the primary antibody (anti-FSHR SAB4501041) diluted in saline, supplemented with 1% BSA for 2 hours at 37° C. At the end of the incubation, the primary antibody is removed by washing with PBS 1× (3 of 5 minutes each) and the cells incubated with the appropriate secondary antibody diluted in PBS 1× supplemented with 1% BSA for 30 min. at 37° C. In this study, a secondary antibody conjugated to cyanine-3 was used (which excited at 550 nm emits a red light at 570 nm). The cells are then washed with PBS 1× (3 washes of 5 min each), the nuclei labeled with DAPI (4',6-diamidin-2-phenylindole) (1:5000, v:v in PBS 1×) (Sigma) for 5 min. at room temperature. The slides are mounted with Elvanol, stored at 4° C. and analyzed by confocal microscope Leica SP5 or by fluorescence microscope LEICA DFC300FX. In the case of treatment with ABRβ1 labeled with NBD, the cells are fixated after washing and immediately prepared for observation in microscopy (as described above) using the pair of filters for observation in the FITC channel.

Analysis of the Cell Growth Curves

CAOV-3 cells were cultured in DMEM supplemented with 10% fetal bovine serum and 2 mM glutamine (Sigma), MDA-MB-231 cells in L15 medium (ATCC) supplemented with 10% fetal bovine serum. OVCAR-3 cells were cultured in RPMI supplemented with 20% fetal bovine serum and 2 mM glutamine and 0.01 mg/ml insulin (Sigma).

Cell cultures are kept in an incubator at 37° C. For the analysis of the growth rate, the cells were seeded onto 6-well plates at a concentration of $5 \times 10^4$ cells/well in the presence of the appropriate medium depending on the cell line. The cells were treated with Gonal-F®, with the ABRβ1 ligand or with both at a concentration of 0.1 μg/ml. The cell growth was evaluated at 24, 48 and 72 hours after the addition of Gonal-F® and ABRβ1 to the culture medium. The cell proliferation rate was evaluated through the cell count, at the indicated times, using the viability test Trypan blue exclusion test.

Analysis of the FSHR Expression in Human Tumor Lines.

The analysis was conducted in flow cytometry using the specific primary antibody developed for human FSHR. The cells were harvested from the culture flasks and kept on ice up to the measurement. Three comparison samples were prepared for each analysis: i) untreated cells, ii) cells incubated with a primary antibody against FSHR developed in rabbit (SAB4501041, Sigma-Aldrich) and with the secondary antibody IgG Alexa Fluor® 488 conjugate anti (TermoFisher), iii) cells incubated alone with the secondary antibody. The preparation of the three experimental conditions allows to assign the signal positivity and exclude any false positives. At the end of the labeling and washing, the cells are analyzed at the FACS. $2 \times 10^5$ events (cells) were acquired and analyzed for each sample.

Binding Analysis of ABRβ1 to FSHR in NB3 Cells (Infant Neuroblastoma Model)

The data obtained by FACS analysis using the ABRβ1 ligand labeled with NBD show that the percentage of labeled cells which thus express FSHR on the cell surface is greater than 96% in all cells analyzed.

Flow Cytometric Analysis of the Internationalization of ABRβ1 Labeled with NBD.

The cells ($4 \times 10^4$ OVCAR-3 or MDA-MB-231) were seeded on 24-well plates 24 hours before the experiment and incubated for 1 hour with increasing concentrations of the fluorescent ABRβ1 ligands. The cells were washed with the Versene solution, detached from the culture plates with trypsin subsequently neutralized by adding 200 μL of FBS. The cells were then centrifuged and re-suspended in Versene solution for flow cytometric measurements. The 488 nm laser was used for fluorophore excitation (ABRβ1 derivatized with NBD).

Analysis of the Accumulation of ABRβ1 in Lysosomes Following Internalization.

The internalization and the subcellular localization of the ligand BRβ1 ligand was performed using confocal microscopy. The cells were seeded on slides for confocal microscopy 24 hours before incubation with the fluorescent ABRβ1 ligand derivatized with Alexa Fluor 647. The cells were co-incubated with the labeled ABRβ1 ligand (250 ng/ml ABRβ1 and LysoTracker Green DND-26, 75 nM) for 1 hour at 37° C. in complete medium. Prior to the acquisition of images, the cells were washed twice with HBSS solution, kept in the same buffer and analyzed immediately in microscopy.

Internalization of ABRβ1 in NB3 Cells

The NB3 cells are cultured in DMEM and seeded on a slide 24 hours before the experiment. The cells were incubated with 150 ng/ml of the ABRβ1 ligand labeled with NBD for 15 minutes in the incubator at 37° C. At the end of the treatment, the cells are washed in saline, incubated in complete culture medium for different periods of time, rinsed in saline and observed under a fluorescence microscope using the pair of filters for FITC. This allows to evaluate the internalization of the fluorescent ABRβ1 in the cells due to the appearance of fluorescent vesicles localized in the cytoplasm.

Analysis of Gonal-F®-Induced cAMP Production and Neutralization with ABRβ1

The analysis used HEK293 cells, in which the exogenous expression of human FSHR (HG15960-UT DBA) and of the biosensor for cyclic AMP-(cAMP), Epac1-camps was obtained through transient co-transfection of genes encoding the two constructs. The analysis used fluorescence microscopy in single living cell, with protocols previously optimized and validated in the laboratory.

The dynamic measurement of intracellular cAMP variations induced by the activation of human FSHR with the agonist Gonal-F® were compared in the absence or presence of the ABRβ1 ligand at various concentrations of use. The analysis of the effect of the ABRβ1 ligand on the internalization dynamics of the FSHR receptor were conducted by immunofluorescence and confocal microscopy. The transfection of HEK293 cells was obtained through Lipofectamine (Invitrogen) according to the manufacturer's instructions, optimized in the laboratory. The co-transfection mixture is obtained by mixing the DNA of Epac2-camps and FSHR in a ratio of 1:1. At the end of the co-transfection procedure, the cells are washed and incubated in DMEM culture medium at 37° C. for 48 hours (to allow the transfected exogenous protein synthesis).

The analysis of the pharmacology of the ABRβ1 molecule was carried out by measuring the change of the intracellular levels of cAMP in viable cells, whose synthesis is very rapid and activated by the FSH receptor activation. The method is based on the expression in a cell of a biosensor based on FRET technology for cAMP (Nikolaev et al. 2006). The biosensor encodes two colors variants of the fluorescent protein GFP connected by a cAMP high-affinity protein domain. The relative intensity of emission of the two GFP variants varies depending on the intracellular concentration of cAMP. The measurement of the fluorescence variation is carried out by fluorescence microscopy in a single cell, by calculating the ratio between the emission intensity in the channel at 480+/−25 nm and in the channel at 535+/−35 nm, depending on the validated sensitized emission ratio method. HEK293 cells were seeded on slides having a 24 mm diameter and transfected to co-express EPAC1-cAMPs and FSHR. The slides are mounted in a small chamber suitable for use with inverted microscopes, for imaging experiments. The culture medium is removed and replaced with Ringer's saline (modified Ringer: 125 NaCl, 5 KCl; 1 Na₃PO₄; 1 MgSO₄; 5.5 Glucose; 20 Hepes; 1.8 CaCl₂, in H₂O, pH 7.4) buffered with Hepes.

In order to determine the cAMP synthesis, the cells were treated with Gonal-F® at concentrations of between 1 and 100 ng/ml. The agonist drug was added directly to the imaging solution after a two-minute acquisition aimed at estimating the baseline FRET levels. In a separate set of experiments, the cAMP measurement was carried out with the same concentrations of Gonal-F® in cells incubated with the ABRβ1 ligand at concentrations ranging from 10-500 ng/ml, for 5 minutes. The image acquisition and analysis was conducted by the Image J software (NIH, Bethesda, MD, USA). The comparison between the experimental groups was performed using the Anova test, considering $P<0.05$ as statistically significant. All data are expressed as mean±SEM.

Those skilled in the art will be able to understand the advantages of the present invention from the above description.

As for the β subunit of FSH, it was surprisingly found that it does not activate the so-called cAMP cascade.

As for the β subunit produced recombinantly, instead, and in particular the ABRβ1 subunit obtained by recombinant technology and expression in *Nicotiana benthamiana*, this has proved to be able to offer many advantages, including: high quality and biological safety, due to the almost zero risk of contamination by viruses, oncogenes, prions, toxins or hazardous reagent residues normally used in the production of therapeutic proteins.

The ability to obtain such an ABRβ1 subunit in a plant host is equally useful and surprising.

In addition, the ABRβ1 subunit has demonstrated a surprising stability, significantly higher even than that of FSH and antibodies.

These advantages were not to the detriment of the activity and affinity towards the FSH receptor; in particular, the affinity was at a nanomolar (nM) level.

A further advantage is that also the ABRβ1 subunit does not activate the FSH receptor, as evidenced by the non-activation of the cAMP cascade.

These properties are particularly surprising and unexpected in the light of a glycosylation pattern different from the glycosylation pattern of the FSHβ subunit of yeast, insect, mammal and, in particular, human cells.

For both FSHβ and ABRβ1 subunits, it was seen that the specific binding with FSHR does not increase the growth rate of cancer cells.

While not activating the receptor, the ABRβ1 showed a significant internalization rate in cells used as a model system.

The prior art described the possible application of peptide fragments of the FSHβ subunit in therapy.

This does not in any way make the therapeutic application of the FSHβ subunit obvious.

In fact, the two structures have significant differences.

For example, the structure of the FSH33-53 peptide, known from Agris et al. (J. Prot. Chem. 1992) includes two turns between the residues 41-46 and 50-52, whereas in the same regions in the FSHβ subunit it has a β-strand conformation. Moreover, the peptide has a small helix region between amino acids 34-36 whereas in the FSHβ-subunit, the same regions are β-strand. Another difference is that cysteine Cys51 forms a disulfide bond in the FSHβ subunit, which bond is absent in the peptide.

An absolutely important advantage of the present invention is the potential application to the treatment and diagnosis of neuroblastoma.

Neuroblastoma is in fact the most common extracranial solid cancer in infant age, which originates from the undifferentiated cells of the neural crest.

It is the most common cancer in children under 1 year and is still widespread in the age group up to 6 years.

The primary tumor is often found in the medulla region of the adrenal gland or in the paraspinous ganglia and unfortunately, at the time of diagnosis, metastasis is already present in more than 50% of cases.

In patients with neuroblastoma, the MYCN oncogene expression analysis (V-Myc Avian Myelocytomatosis Viral Oncogene Neuroblastoma) is positive in 20% of cases and this correlates closely with the high risk of fatal prognosis.

Currently, MYCN amplification represents the best genetic marker for risk allocation in neuroblastoma.

The allocation of the mortality risk is based on the integration of several clinical and biological factors, including the advancement stage of neuroblastoma (Brodeur et al. 1993), the age at diagnosis (Brodeur et al. 1988), the amplification of MYCN (Seeger et al. 1985) and the histological examination (Shimada et al. 1984).

Among all these criteria, age and early diagnosis are the most important variables for the allocation of risk in metastatic patients.

The intermediate risk group includes patients who are diagnosed before their first year of life.

Patients with delay in diagnosis are instead included in the high-risk class, whereas low- and medium-risk patients generally have favorable prognosis with a survival rate of about 80%.

The situation is extremely unfavorable in high-risk patients where the survival rate drops below 40%.

Moreover, a "very high risk" class of patients has been recently identified in which there is no response to anticancer therapy or relapses occur with a high probability (Maris et al. 2007; Matthay et al. 2012).

The therapies currently being studied for the treatment of neuroblastoma are based on radiolabeled molecules which are captured by the tumor in a preferential manner with respect to healthy tissues, on immunotherapy which uses monoclonal antibodies against surface tumor antigens and on synthetic inhibitors of kinases which control the cell cycle.

However, due to the instability of antibodies and the limited specificity of other molecules for the tumor tissue, significant side effects occur in patients, which limit the effectiveness of treatment protocols (Matthay et al. 2012b).

The present invention may represent a promising alternative to the currently available treatments.

---

The invention claimed is:

1. A ligand of human follicle stimulating hormone receptor (FSHR) for medical use comprising SEQ ID NO: 2.

2. The ligand of human FSHR according to claim 1, wherein the ligand comprises the amino acid sequence of SEQ ID NO: 2 encoded by SEQ ID NO: 3.

3. The ligand of human FSHR according to claim 1, wherein the ligand comprises glycosylation sites at the asparagine residues N13 and N30 of SEQ ID NO: 2, and wherein each of the glycosylation sites comprises two N-acetylglucosamine residues and at least one mannose residue.

4. The ligand of human FSHR according to claim 1, wherein the ligand is for treatment, diagnosis, or treatment and diagnosis, of tumors; and wherein the tumors are one or more of ovarian cancer, breast cancer, or neuroblastoma.

5. The ligand of human FSHR according to claim 4, wherein the ligand is conjugated to a molecule having anti-tumor activity selected from the group consisting of cytotoxic agents, alkylating agents, protein synthesis modulators, mitotic inhibitors, and β-emitting radioisotopes.

6. The ligand of human FSHR according to claim 4, wherein the ligand in conjugated or non-conjugated form is in combination with one or more agents with anti-tumor activity.

7. The ligand of human FSHR according to claim 4, wherein the ligand is for diagnosis of tumors; and wherein the ligand is conjugated to:
   fluorescent molecule selected from the group consisting of fluorescein isothiocyanate (FITC), phycoerythrin (PE) and indocyanine; or
   radioactive molecule selected from the group consisting of $^{123}$I, $^{111}$In, $^{188}$Re, $^{18}$F, $^{35}$S, and $^{99}$Tc.

8. The ligand of human FSHR according to claim 4, wherein said tumor is in a pediatric patient.

9. The ligand of human FSHR according to claim 1, wherein the ligand is conjugated to a molecule having anti-tumor activity selected from the group consisting of cytotoxic agents, alkylating agents, protein synthesis modulators, mitotic inhibitors and β-emitting radioisotopes.

10. The ligand of claim 9, wherein the cytotoxic agent is a pyrimidine antagonist or enzyme inhibitor.

11. The ligand of claim 10, wherein the pyrimidine antagonist is capecitabine.

12. The ligand of human FSHR according to claim 1, wherein the ligand is obtained by expression from a vector comprising SEQ ID NO: 3 in one or more *Nicotiana benthamiana* cells.

13. The ligand of human FSHR according to claim 1, wherein the ligand is for treatment of neuroblastoma, and wherein the ligand in the conjugated or non-conjugated form is in combination with one or agents having anti-tumor activity.

14. A pharmaceutical composition comprising the ligand of human FSHR according to claim 1 and one or more pharmaceutically acceptable carriers and/or excipients.

15. The pharmaceutical composition according to claim 14, wherein the pharmaceutical composition is formulated for intravenous administration.

16. A method for preparing the ligand of human FSHR according to claim 1, wherein the method comprises attaching the amino acid sequence KDEL (SEQ ID NO: 14) to the C-terminus of β subunit of human follicle stimulating hormone (FSHβ).

17. The method according to claim 16, wherein the method further comprises attaching a His-taq to the N-terminus of the β subunit of human follicle stimulating hormone (FSHβ).

18. A ligand of human FSHR comprising the amino acid sequence that is at least 97% identical to SEQ ID NO: 2.

19. The ligand of human FSHR according to claim 18, wherein the ligand is conjugated to a molecule having diagnostic activity selected from the group consisting of:
   fluorescent molecule selected from the group consisting of fluorescein isothiocyanate (FITC), phycoerythrin (PE) and indocyanine; or
   radioactive molecule selected from the group consisting of $^{123}$I, $^{111}$In, $^{188}$Re, $^{18}$F, $^{35}$S, and $^{99}$Tc.

* * * * *